US012698327B2

(12) United States Patent
Li et al.

(10) Patent No.: US 12,698,327 B2
(45) Date of Patent: Aug. 4, 2026

(54) Anti-TIGIT ANTIBODY, AND PHARMACEUTICAL COMPOSITION AND USE THEREOF

(71) Applicant: AKESO BIOPHARMA, INC., Zhongshan (CN)

(72) Inventors: Baiyong Li, Zhongshan (CN); Yu Xia, Zhongshan (CN); Zhongmin Wang, Zhongshan (CN); Peng Zhang, Zhongshan (CN)

(73) Assignee: AKESO BIOPHARMA, INC., Zhongshan (CN)

( * ) Notice: Subject to any disclaimer, the term of this patent is extended or adjusted under 35 U.S.C. 154(b) by 619 days.

(21) Appl. No.: 18/250,440

(22) PCT Filed: Oct. 26, 2021

(86) PCT No.: PCT/CN2021/126277
§ 371 (c)(1),
(2) Date: Apr. 25, 2023

(87) PCT Pub. No.: WO2022/089392
PCT Pub. Date: May 5, 2022

(65) Prior Publication Data
US 2024/0002504 A1 Jan. 4, 2024

(30) Foreign Application Priority Data
Oct. 26, 2020 (CN) .......................... 202011153458.2

(51) Int. Cl.
| | |
|---|---|
| *C07K 16/28* | (2006.01) |
| *A61K 39/00* | (2006.01) |
| *A61P 35/00* | (2006.01) |
| *C12N 15/63* | (2006.01) |

(52) U.S. Cl.
CPC .......... *C07K 16/2803* (2013.01); *A61K 39/00* (2013.01); *A61P 35/00* (2018.01); *C12N 15/63* (2013.01); *C07K 2317/24* (2013.01); *C07K 2317/31* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2016/0176963 A1 | 6/2016 | Maurer et al. |
| 2017/0088613 A1 | 3/2017 | Grogan et al. |
| 2017/0281764 A1 | 10/2017 | Tso et al. |
| 2019/0100591 A1 | 4/2019 | Cooper et al. |
| 2024/0352153 A1 | 10/2024 | Wang et al. |

FOREIGN PATENT DOCUMENTS

| | | |
|---|---|---|
| CN | 107207594 A | 9/2017 |
| CN | 108290946 A | 7/2018 |
| CN | 108883164 A | 11/2018 |
| CN | 109206523 A | 1/2019 |
| CN | 109384846 A | 2/2019 |
| CN | 109734806 A | 5/2019 |
| CN | 110818795 A | 2/2020 |
| CN | 110997720 A | 4/2020 |
| CN | 111196852 A | 5/2020 |
| CN | 111705066 A | 9/2020 |
| CN | 111744013 A | 10/2020 |
| EP | 4089115 A1 | 11/2022 |
| EP | 4389771 A1 | 6/2024 |
| WO | 2016191643 A2 | 12/2016 |
| WO | 2017053748 A2 | 3/2017 |
| WO | 2017152088 A1 | 9/2017 |
| WO | 2019165434 A1 | 8/2019 |
| WO | 2023001303 A1 | 1/2023 |
| WO | 2023020625 A1 | 2/2023 |

OTHER PUBLICATIONS

Taylor N.P., Roche's TIGIT prospect fails another phase 3 lung cancer test. Biotech, Nov. 26, 2024. (Year: 2024).*
Taylor N.P., Merck stops phase 3 TIGIT trial in lung cancer for futility—and sees immune side effects again. Biotech, Aug. 8, 2024. (Year: 2024).*
Manalac, T., Four Therapies Hanging on the Troubled TIGIT Space. BioSpace, 2025. (Year: 2025).*
Chen et al. TIGIT enhances CD4+ regulatory T-cell response and mediates immune suppression in a murine ovarian cancer model. CCancer Medicine, 2020; 9:3584-3591. (Year: 2020).*
Guillerey et al. TIGIT immune checkpoint blockade restores CD8⁺ T-cell immunity against multiple myeloma. Blood. 2018; 132(16): 1689-1694. (Year: 2018).*
International Search Report and Written Opinion of PCT/CN2021/126277, mailed on Jan. 26, 2022, 25 pages.
Zhong et al., "Two Types of Anti-Tigit Antibodies with Distinct Binding Epitope and Functional Activities," Journal for Immuno Therapy of Cancer, 2020, 8(3):A109.
Guohua et al., "Preparation and Activity Identification of Anti-TIGIT Monoclonal Antibody," J Med Mol Biol, 2020, 17(1):052-056.

(Continued)

*Primary Examiner* — Maher M Haddad
(74) *Attorney, Agent, or Firm* — HESLIN ROTHENBERG FARLEY & MESITI P.C.

(57) ABSTRACT

An ant-TIGIT antibody, and a pharmaceutical composition and the use thereof. The present invention relates to an anti-TIGIT antibody or an antigen-binding fragment thereof, wherein a heavy chain variable region of the antibody comprises HCDR1-HCDR3 having amino acid sequences as shown in SEQ ID NOs: 3-5, respectively; and a light chain variable region of the antibody comprises LCDR1-LCDR3 having amino acid sequences as shown in SEQ ID NOs: 8-10, respectively. The antibody can effectively bind to TIGIT and has the potential for use in tumor prevention and treatment.

29 Claims, 13 Drawing Sheets
Specification includes a Sequence Listing.

(56) References Cited

OTHER PUBLICATIONS

Dolgin, "Antiobody engineers seek optimal drug targeting TIGIT checkpoint," Nature Biotechnology, 2020, 38:1007-1015.

Ma et al., "A novel bispecific nanobody with PD-L1/TIGIT dual immune checkpoint blockade," Biochemical and Biophysical Research Communications, 2020, 531(2):144-151.

Rodriguez-Abreu, Delvys, et al.; "Primary analysis of a randomized, double-blind, phase II study of the anti-TIGIT antibody tiragolumab (tira) plus atezolizumab (atezo) versus placebo plus atezo as first-line (1L) treatment in patients with PD-L1-selected NSCLC (Cityscape)."; Journal of Clinical Oncology 2020; 38(15):1-4.

Extended European Search Report for EP Application No. 21 885 119.4 dated Sep. 13, 2024.

* cited by examiner

CD155

1

Anti-TIGIT ANTIBODY, AND PHARMACEUTICAL COMPOSITION AND USE THEREOF

CROSS REFERENCE TO RELATED APPLICATIONS

This application is a national stage filing under Section 371 of International Application No. PCT/CN2021/126277, filed on Oct. 26, 2021, and which claims priority to Chinese Patent Application No. 202011153458.2 filed on Oct. 26, 2020, the entire disclosures of which applications are hereby incorporated by reference herein in their entireties.

SEQUENCE LISTING

The instant application contains an electronic sequence listing. The contents of the electronic sequence listing H2651048.txt; Size: 18,142 bytes; and Date of Creation: Apr. 21, 2023 is herein incorporated by reference in its entirety.

TECHNICAL FIELD

The present invention belongs to the field of pharmaceutics, and relates to an anti-TIGIT antibody, a pharmaceutical composition thereof, and use thereof. More particularly, the present invention relates to an anti-TIGIT monoclonal antibody.

BACKGROUND

TIGIT (T cell Ig and ITIM domain, also known as WUCAM, Vstm3, or VSIG9) is a member of the poliovirus receptor (PVR)/Nectin family. TIGIT consists of an extracellular immunoglobulin variable region (IgV) domain, a type I transmembrane domain, and an intracellular domain with a classical immunoreceptor tyrosine-based inhibitory motif (ITIM) and an immunoglobulin tail tyrosine (ITT) motif. TIGIT is highly expressed in lymphocytes, especially in effector and regulatory CD4+ T cells, follicular helper CD4+ T cells and effector CD8+ T cells, as well as natural killer (NK) cells (Yu X, Harden K, Gonzalez L C, et al. The surface protein TIGIT suppresses T cell activation by promoting the generation of mature immunoregulatory dendritic cells[J]. *Nature immunology*, 2009, 10(1): 48).

CD155 (also known as PVR, Necl5 or Tage4), CD112 (also known as PVRL2/nectin 2) and CD113 (also known as PVRL3) are ligands to which TIGIT binds (Martinet L, Smyth M J. Balancing natural killer cell activation through paired receptors[J]. *Nature Reviews Immunology*, 2015, 15(4): 243-254), and CD155 is a high-affinity ligand for TIGIT. In NK cells, TIGIT binding to ligands CD155 and CD112 can inhibit the killing effect of NK cells on TIGIT high expression cells (Stanietsky N, Simic H, Arapovic J, et al. The interaction of TIGIT with PVR and PVRL2 inhibits human NK cell cytotoxicity[J]. *Proceedings of the National Academy of Sciences*, 2009, 106(42): 17858-17863). It was reported that the killing effect of CD8+ T cells can be enhanced when PD-1 and TIGIT are blocked simultaneously (Johnston R J, Comps-Agrar L, Hackney J, et al. The immunoreceptor TIGIT regulates antitumor and antiviral CD8+ T cell effector function[J]. *Cancer cell*, 2014, 26(6): 923-937). Recent research revealed that the inhibitory receptor TIGIT, as an immune checkpoint of NK cells, can cause NK cell exhaustion in the process of tumor development, and proved that anti-TIGIT monoclonal antibodies can reverse NK cell exhaustion and be used for immunotherapy of a variety of tumors such as non-small cell lung cancer, small cell lung cancer, breast cancer, ovarian cancer, colorectal cancer, melanoma, pancreatic cancer, cervical tumor, multiple myeloma, non-Hodgkin's lymphoma, B-lymphoma, and plasma cell cancer (Zhang Q, Bi J, Zheng X, et al. Blockade of the checkpoint receptor TIGIT prevents NK cell exhaustion and elicits potent anti-tumor immunity[J]. *Nature immunology*, 2018, 19(7): 723-732).

The TIGIT and CD155 expression levels in cancer tissues of hepatocellular carcinoma (HCC) patients are up-regulated as the degree of carcinogenesis descends. The frequencies of TIGIT+ CD4+ T cells and TIGIT+ Treg cells in the peripheral blood of patients decreased after HCC surgery. The increase in TIGIT expression was positively correlated with the AFP level. These results indicate that the co-inhibitory receptor TIGIT may be involved in the pathogenesis of HCC and represent a new target for diagnosis and treatment of HCC (Duan Xiangguo, Liu Juanxi, Cui Jianjian et al. Expression of TIGIT/CD155 and correlations with clinical pathological features in human hepatocellular carcinoma[J]. *Mol Med Rep*, 2019, 20: 3773-3781).

In addition, it was reported that TIGIT blockers alone or in combination with PD-1 blockers plus CD96 blockers significantly reduce the growth of B16 melanoma in wild-type and CD155-/- mouse models (Li X-Y, Das I, Lepletier A, et al. CD155 loss enhances tumor suppression via combined host and tumor-intrinsic mechanisms. *J Clin Invest*, 2018, 128: 2613-25). CD112R blocker alone or in combination with TIGIT blockers and/or PD-1 blockers increases cytokine production ability of TILs in ovarian cancer, endometrial cancer and lung tumor (Whelan S, Ophir E, Kotturi M F, et al. PVRIG and PVRL2 electrode Induced in Cancer and Inhibit CD8+ T-cell function. *Cancer Immunol Res*, 2019, 7: 257-68).

Anti-TIGIT antibody medicaments as new immune checkpoint antibody medicaments have promising utility in a variety of applications, and can be used for immunotherapy of tumors. Tiragolumab developed by Roche is now in phase 3 clinical trials, and it was reported that the combination of the TIGIT monoclonal antibody Tiragolumab and the PD-L1 medicament Tecentriq (Atezolizumab) as a first-line therapy was well tolerated in patients with PD-L1-positive metastatic non-small cell lung cancer (NSCLC) in phase 2 clinical trials and had a significant effect—a 43% reduction in the risk of disease progression (Exit C. Roche to present first clinical data on novel anti-TIGIT cancer immunotherapy tiragolumab at ASCO[J]).

However, the affinity of existing anti-human TIGIT antibody medicaments is low; there is still a need for anti-TIGIT antibodies with high affinity.

Therefore, the development of antibody medicaments with high affinity for TIGIT, higher efficacy and fewer toxic side effects for treating autoimmune diseases is of great significance.

SUMMARY

After intensive studies and creative efforts, the inventors used mammalian cell expression systems to express recombinant human TIGIT as an antigen to immunize mice, and obtained hybridoma cells by fusion of mouse spleen cells and myeloma cells. The inventor obtained a hybridoma cell line LT019 (deposited under CCTCC NO. C2020208) by screening a large number of samples.

The inventors surprisingly found that the hybridoma cell line LT019 can secrete a specific monoclonal antibody (designated 26B12) specifically binding to human TIGIT, and the monoclonal antibody can effectively bind to TIGIT, reduce the inhibitory effect of TIGIT on immune cells, promote the activity of T cells, reverse NK cell exhaustion, and enhance the killing effect of immune cells on a tumor. Further, the inventors have creatively prepared humanized anti-human TIGIT antibodies (designated 26B12H1L1, 26B12H4L1, 26B12H2L2, 26B12H3L2, 26B12H2L3, 26B12H3L3, 26B12H1L4, and 26B12H4L4).

The inventors also surprisingly found that antibodies 26B12H1L1, 26B12H4L1, 26B12H2L2, 26B12H3L2, 26B12H2L3, 26B12H3L3, 26B12H1L4, and 26B12H4L4 of the present invention have binding activity to TIGIT and have strong affinity; 26B12H1L1, 26B12H4L1, 26B12H2L2, 26B12H3L2, 26B12H2L3, 26B12H3L3, 26B12H1L4, and 26B12H4L4 can effectively reduce the activity of TIGIT. The antibodies of the present invention have the potential to treat and/or prevent diseases such as tumors (e.g., liver cancer, kidney cancer, brain tumor, urothelial carcinoma, bone tumor, cholangiocarcinoma, non-small cell lung cancer, small cell lung cancer, breast cancer, ovarian cancer, colorectal cancer, melanoma, pancreatic cancer, cervical tumor, multiple myeloma, Hodgkin's lymphoma, non-Hodgkin's lymphoma, B-lymphoma, ovarian cancer, plasma cell cancer, endometrial cancer, prostate cancer, and testicular cancer). The present invention is detailed below.

One aspect of the present invention relates to an anti-TIGIT antibody or an antigen-binding fragment thereof, wherein a heavy chain variable region of the antibody comprises HCDR1-HCDR3 with amino acid sequences set forth in SEQ ID NOs: 3-5, respectively, and a light chain variable region of the antibody comprises LCDR1-LCDR3 with amino acid sequences set forth in SEQ ID NOs: 8-10, respectively.

In one or more embodiments of the present invention, the anti-TIGIT antibody or the antigen-binding fragment thereof is provided, wherein the heavy chain variable region of the antibody comprises an amino acid sequence selected from SEQ ID NO: 1, SEQ ID NO: 11, SEQ ID NO: 13, SEQ ID NO: 15, and SEQ ID NO: 17; and the light chain variable region of the antibody comprises an amino acid sequence selected from SEQ ID NO: 6, SEQ ID NO: 19, SEQ ID NO: 21, SEQ ID NO: 23, and SEQ ID NO: 25.

In one or more embodiments of the present invention, the ant-TIGIT antibody or the antigen-binding fragment thereof is provided, wherein the heavy chain variable region of the antibody comprises an amino acid sequence set forth in SEQ ID NO: 1, and the light chain variable region of the antibody comprises an amino acid sequence set forth in SEQ ID NO: 6;

the heavy chain variable region of the antibody comprises an amino acid sequence set forth in SEQ ID NO: 11, and the light chain variable region of the antibody comprises an amino acid sequence set forth in SEQ ID NO: 19;

the heavy chain variable region of the antibody comprises an amino acid sequence set forth in SEQ ID NO: 17, and the light chain variable region of the antibody comprises an amino acid sequence set forth in SEQ ID NO: 19;

the heavy chain variable region of the antibody comprises an amino acid sequence set forth in SEQ ID NO: 13, and the light chain variable region of the antibody comprises an amino acid sequence set forth in SEQ ID NO: 21;

the heavy chain variable region of the antibody comprises an amino acid sequence set forth in SEQ ID NO: 13, and the light chain variable region of the antibody comprises an amino acid sequence set forth in SEQ ID NO: 23;

the heavy chain variable region of the antibody comprises an amino acid sequence set forth in SEQ ID NO: 15, and the light chain variable region of the antibody comprises an amino acid sequence set forth in SEQ ID NO: 21;

the heavy chain variable region of the antibody comprises an amino acid sequence set forth in SEQ ID NO: 15, and the light chain variable region of the antibody comprises an amino acid sequence set forth in SEQ ID NO: 23;

the heavy chain variable region of the antibody comprises an amino acid sequence set forth in SEQ ID NO: 11, and the light chain variable region of the antibody comprises an amino acid sequence set forth in SEQ ID NO: 25; or the heavy chain variable region of the antibody comprises an amino acid sequence set forth in SEQ ID NO: 17, and the light chain variable region of the antibody comprises an amino acid sequence set forth in SEQ ID NO: 25.

In one or more embodiments of the present invention, the ant-TIGIT antibody or the antigen-binding fragment thereof is provided, wherein the antibody comprises a non-CDR region derived from a species other than murine, such as from a human antibody.

In one or more embodiments of the present invention, the ant-TIGIT antibody or the antigen-binding fragment thereof is provided, wherein a heavy chain constant region of the antibody is Ig gamma-1 chain C region (e.g., NCBI ACCESSION: P01857), or Ig gamma-4 chain C region (e.g., NCBI ACCESSION: P01861.1); a light chain constant region of the antibody is Ig kappa chain C region (e.g., NCBI ACCESSION: P01834).

In one or more embodiments of the present invention, the anti-TIGIT antibody or the antigen-binding fragment thereof is provided, wherein the anti-TIGIT antibody or the antigen-binding fragment thereof is selected from Fab, Fab', F(ab')2, Fd, Fv, dAb, a complementarity determining region fragment, a single chain antibody, a humanized antibody, a chimeric antibody, and a diabody.

In one or more embodiments of the present invention, the ant-TIGIT antibody or the antigen-binding fragment thereof is provided, wherein the antibody binds to TIGIT-mFc with a $K_D$ of less than 4E-10 or less than 4E-11; preferably, the $K_D$ is measured by a Fortebio molecular interaction instrument.

In one or more embodiments of the present invention, the anti-TIGIT antibody or the antigen-binding fragment thereof is provided, wherein the antibody binds to TIGIT-mFc with an $EC_{50}$ of less than 1.5 nM, less than 1.2 nM, or less than 1 nM; preferably, the $EC_{50}$ is measured by a flow cytometer.

In some embodiments of the present invention, the anti-TIGIT antibody is a monoclonal antibody.

In some embodiments of the present invention, the anti-TIGIT antibody is a humanized antibody, a chimeric antibody or a multispecific antibody (e.g., a bispecific antibody).

In some embodiments of the present invention, the antigen-binding fragment is selected from Fab, Fab', F(ab')$_2$, Fd, Fv, dAb, Fab/c, a complementarity determining region fragment, a single chain antibody (e.g., scFv), a humanized antibody, a chimeric antibody and a bispecific antibody.

In one or more embodiments of the present invention, the anti-TIGIT antibody or the antigen-binding fragment thereof is provided, wherein the antibody is an antibody produced by a hybridoma cell line LT019 deposited at China Center for Type Culture Collection (CCTCC) under CCTCC NO. C2020208.

Another aspect of the present invention relates to an isolated nucleic acid molecule encoding any of the ant-TIGIT antibodies or the antigen-binding fragments thereof according to the present invention.

Yet another aspect of the present invention relates to a vector comprising the isolated nucleic acid molecule of the present invention.

Yet another aspect of the present invention relates to a host cell comprising the isolated nucleic acid molecule of the present invention or the vector of the present invention.

Yet another aspect of the present invention relates to a hybridoma cell line LT019 deposited at China Center for Type Culture Collection (CCTCC) under CCTCC NO. C2020208.

Yet another aspect of the present invention relates to a conjugate comprising an antibody and a conjugated moiety, wherein the antibody is any of the anti-TIGIT antibodies or the antigen-binding fragments thereof according to the present invention, and the conjugated moiety is a detectable label; preferably, the conjugated moiety is a radioisotope, a fluorescent substance, a luminescent substance, a colored substance, or an enzyme.

Yet another aspect of the present invention relates to a kit comprising any of the anti-TIGIT antibodies or the antigen-binding fragments thereof according to the present invention or comprising the conjugate of the present invention;

preferably, the kit further comprises a secondary antibody specifically recognizing the antibody; optionally, the secondary antibody further comprises a detectable label, for example, a radioisotope, a fluorescent substance, a luminescent substance, a colored substance, or an enzyme.

Yet another aspect of the present invention relates to use of any of the antibodies according to the present invention or the conjugate of the present invention in preparing a kit for detecting the presence or level of TIGIT in a sample.

Yet another aspect of the present invention relates to a pharmaceutical composition comprising any of the anti-TIGIT antibodies or the antigen-binding fragments thereof according to the present invention or the conjugate of the present invention; optionally, the pharmaceutical composition further comprises a pharmaceutically acceptable carrier and/or excipient.

In one or more embodiments of the present invention, the pharmaceutical composition further comprises one or more anti-PD-1 antibodies, or one or more anti-PD-L1 antibodies.

In one or more embodiments of the present invention, the pharmaceutical composition is provided, wherein the mass ratio of the anti-TIGIT antibody or the antigen-binding fragment thereof to the anti-PD-1 antibody or the anti-PD-L1 antibody is (1:5)-(5:1), e.g., 1:5, 1:4, 1:3, 1:2, 1:1, 2:1, 3:1, 4:1 or 5:1, based on the mass of the antibodies.

Yet another aspect of the present invention relates to a bispecific antibody comprising a first protein functional region and a second protein functional region, wherein:

the first protein functional region targets TIGIT;

the second protein functional region targets a target other than TIGIT (e.g., PD-1);

wherein the first protein functional region is any of the antibodies or the antigen-binding fragments according to the present invention;

preferably, the bispecific antibody is in IgG-scFv format;

preferably, the first protein functional region is any of the antibodies according to the present invention and is in immunoglobulin form, and the second protein functional region is a single chain antibody; or preferably, the first protein functional region is a single chain antibody, and the second protein functional region is an antibody in immunoglobulin form.

In some embodiments of the present invention, the bispecific antibody is provided, wherein any of the antibodies according to the present invention is in immunoglobulin form.

In some embodiments of the present invention, the bispecific antibody is provided, wherein the single chain antibody is in the form of heavy chain variable region-linker fragment-light chain variable region.

In some embodiments of the present invention, the bispecific antibody is provided, wherein the first protein functional region and the second protein functional region are linked directly or via a linker fragment; the linker fragment and the above-mentioned linker fragment in the single chain antibody may be identical or different and may be linker fragments commonly used in the art.

In some embodiments of the present invention, the bispecific antibody is provided, wherein the numbers of the first protein functional region and the second protein functional region are each independently 1, 2 or more.

In some embodiments of the present invention, the bispecific antibody is provided, wherein the single chain antibody is linked to the C-termini of the two heavy chains of the antibody in immunoglobulin form; preferably, each heavy chain is linked to a single chain antibody.

Yet another aspect of the present invention relates to a combination product comprising a first product and a second product in separate packages, wherein the first product comprises any of the ant-TIGIT antibodies or the antigen-binding fragments thereof according to the present invention, the conjugate of the present invention, or any of the pharmaceutical compositions according to the present invention; the second product comprises at least one anti-PD-1 antibody or at least one anti-PD-L1 antibody;

preferably, the first product and the second product further independently comprise one or more pharmaceutically acceptable adjuvants (e.g., carriers and/or excipients);

preferably, the combination product further comprises a package insert.

In one or more embodiments of the present invention, the combination product is provided, wherein the mass ratio of the anti-TIGIT antibody or the antigen-binding fragment thereof to the anti-PD-1 antibody or the anti-PD-L1 antibody is (1:5)-(5:1), e.g., 1:5, 1:4, 1:3, 1:2, 1:1, 2:1, 3:1, 4:1 or 5:1, based on the mass of the antibodies.

Yet another aspect of the present invention relates to use of any of the antibodies or the antigen-binding fragments thereof according to the present invention, the conjugate of the present invention, any of the bispecific antibodies according to the present invention, any of the pharmaceutical compositions according to the present invention, or any of the combination products according to the present invention in preparing a medicament for treating and/or preventing a tumor; preferably, the tumor is selected from one or more of liver cancer, kidney cancer, brain tumor, urothelial carcinoma, bone tumor, cholangiocarcinoma, non-small cell lung cancer, small cell lung cancer, breast cancer, ovarian cancer, colorectal cancer, melanoma, pancreatic cancer, cervical tumor, multiple myeloma, Hodgkin's lymphoma, non-Hodgkin's lymphoma, B-lymphoma, ovarian cancer, plasma cell cancer, endometrial cancer, prostate cancer, and testicular cancer.

Any of the antibodies or the antigen-binding fragments thereof according to the present invention, the conjugate of the present invention, any of the bispecific antibodies according to the present invention, any of the pharmaceutical compositions according to the present invention, or any of the combination products according to the present invention is provided for use in treating and/or preventing a tumor; preferably, the tumor is selected from one or more of liver cancer, kidney cancer, brain tumor, urothelial carcinoma, bone tumor, cholangiocarcinoma, non-small cell lung cancer, small cell lung cancer, breast cancer, ovarian cancer, colorectal cancer, melanoma, pancreatic cancer, cervical tumor, multiple myeloma, Hodgkin's lymphoma, non-Hodgkin's lymphoma, B-lymphoma, ovarian cancer, plasma cell cancer, endometrial cancer, prostate cancer, and testicular cancer.

Yet another aspect of the present invention relates to a method for treating and/or preventing a tumor, and the method comprises the step of administering to a subject in need an effective amount of any of the antibodies or the antigen-binding fragments thereof according to the present invention, the conjugate of the present invention, any of the bispecific antibodies according to the present invention, any of the pharmaceutical compositions according to the present invention, or any of the combination products according to the present invention; preferably, the tumor is selected from one or more of liver cancer, kidney cancer, brain tumor, urothelial carcinoma, bone tumor, cholangiocarcinoma, non-small cell lung cancer, small cell lung cancer, breast cancer, ovarian cancer, colorectal cancer, melanoma, pancreatic cancer, cervical tumor, multiple myeloma, Hodgkin's lymphoma, non-Hodgkin's lymphoma, B-lymphoma, ovarian cancer, plasma cell cancer, endometrial cancer, prostate cancer, and testicular cancer.

In some embodiments of the present invention, the liver cancer is hepatocellular carcinoma.

The variable regions of the light chain and the heavy chain determine antigen binding; the variable region of each chain contains three hypervariable regions called complementarity determining regions (CDRs) (CDRs of the heavy chain (H) include HCDR1, HCDR2 and HCDR3, and CDRs of the light chain (L) include LCDR1, LCDR2 and LCDR3, which are named by Kabat et al., see Bethesda M.d., *Sequences of Proteins of Immunological Interest*, Fifth Edition, NIH Publication 1991; 1-3:91-3242).

Preferably, CDRs may also be defined by the IMGT numbering system, see Ehrenmann, Francois, Quentin Kaas, and Marie-Paule Lefranc. IMGT/3Dstructure-DB and IMGT/DomainGapAlign: a database and a tool for immunoglobulins or antibodies, T cell receptors, MHC, IgSF and MhcSF. *Nucleic acids research* 2009; 38(suppl_1): D301-D307.

The amino acid sequences of the CDRs of the monoclonal antibody sequences are analyzed according to the IMGT definition by technical means well known to those skilled in the art, for example by using the VBASE2 database.

The antibodies 26B12, 26B12H1L1, 26B12H4L1, 26B12H2L2, 26B12H3L2, 26B12H2L3, 26B12H3L3, 26B12H1L4 and 26B12H4L4 involved in the present invention have the same CDRs:

the 3 CDRs of their heavy chain variable regions have the following amino acid sequences:

```
HCDR1:
                                    (SEQ ID NO: 3)
GHSFTSDYA

HCDR2:
                                    (SEQ ID NO: 4)
ISYSDST

HCDR3:
                                    (SEQ ID NO: 5)
ARLDYGNYGGAMDY;
``` the 3 CDRs of their light chain variable regions have the following amino acid sequences:

```
LCDR1:
                                    (SEQ ID NO: 8)
QHVSTA

LCDR2:
                                    (SEQ ID NO: 9)
SAS

LCDR3:
                                    (SEQ ID NO: 10)
QQHYITPWT.
```

In the present invention, unless otherwise defined, the scientific and technical terms used herein have the meanings generally understood by those skilled in the art. In addition, the laboratory operations of cell culture, molecular genetics, nucleic acid chemistry and immunology used herein are the routine procedures widely used in the corresponding fields. Meanwhile, in order to better understand the present invention, the definitions and explanations of the relevant terms are provided below.

As used herein, when referring to the amino acid sequence of TIGIT (NCBI GenBank ID: NP_776160.2), it includes the full length of TIGIT protein, or an extracellular immunoglobulin variable region (IgV) domain or a fragment comprising an extracellular immunoglobulin variable region (IgV) domain; also included are fusion proteins of TIGIT, such as a fragment fused to an Fc protein fragment of a mouse or human IgG (mFc or hFc). However, those skilled in the art will appreciate that in the amino acid sequence of the TIGIT protein, mutations or variations (including but not limited to, substitutions, deletions and/or additions) may naturally occur or can be artificially introduced without affecting biological functions thereof. Therefore, in the present invention, the term "TIGIT protein" or "TIGIT" shall include all such sequences, including the sequences set forth and natural or artificial variants thereof. Moreover, when describing the sequence fragment of the TIGIT protein, it includes not only the sequence fragment but also a corresponding sequence fragment in natural or artificial variants thereof.

As used herein, the term $EC_{50}$ refers to the concentration for 50% of maximal effect, i.e., the concentration that can cause 50% of the maximal effect.

As used herein, the term "antibody" refers to an immunoglobulin molecule that generally consists of two pairs of polypeptide chains (each pair with one "light" (L) chain and one "heavy" (H) chain). Antibody light chains are classified into κ and α light chains. Heavy chains are classified into μ, δ, γ, α, or ε. Isotypes of antibodies are defined as IgM, IgD, IgG, IgA, and IgE. In light chains and heavy chains, the variable region and constant region are linked by a "J"

region of about 12 or more amino acids, and the heavy chain further comprises a "D" region of about 3 or more amino acids. Each heavy chain consists of a heavy chain variable region ($V_H$) and a heavy chain constant region ($C_H$). The heavy chain constant region consists of 3 domains ($C_{H1}$, $C_{H2}$, and $C_{H3}$).

Each light chain consists of a light chain variable region ($V_L$) and a light chain constant region ($C_L$). The light chain constant region consists of one domain $C_L$. The constant region of the antibody can mediate the binding of immunoglobulins to host tissues or factors, including the binding of various cells of the immune system (e.g., effector cells) to the first component (C1q) of classical complement system. The $V_H$ and $V_L$ regions can be further subdivided into hypervariable regions (called complementarity determining regions, or CDRs) and conservative regions called framework regions (FRs) that are distributed between the CDRs. Each $V_H$ and $V_L$ consists of 3 CDRs and 4 FRs arranged from the amino terminus to the carboxyl terminus in the following order: FR1, CDR1, FR2, CDR2, FR3, CDR3, FR4. The variable regions ($V_H$ and $V_L$) of each heavy chain/light chain pair form antigen-binding sites, respectively. The assignment of amino acids to the regions or domains is based on Kabat Sequences of Proteins of Immunological Interest (National Institutes of Health, Bethesda, M.d. (1987 and 1991)), or Chothia & Lesk *J. Mol. Biol.* 1987; 196:901-917; Chothia et al. *Nature* 1989; 342:878-883 or the definition of the IMGT numbering system, see the definition in Ehrenmann, Francois, Quentin Kaas, and Marie-Paule Lefranc. "IMGT/3Dstructure-DB and IMGT/DomainGapAlign: a database and a tool for immunoglobulins or antibodies, T cell receptors, MHC, IgSF and MhcSF." *Nucleic acids research* 2009; 38(suppl_1): D301-D307. The term "antibody" is not limited by any specific method for producing the antibody. For example, the antibody includes, in particular, a recombinant antibody, a monoclonal antibody and a polyclonal antibody. The antibody can be antibodies of different isotypes, such as IgG (e.g., subtypes IgG1, IgG2, IgG3 or IgG4), IgA1, IgA2, IgD, IgE or IgM.

As used herein, the term "antigen-binding fragment", also known as the "antigen-binding portion", refers to a polypeptide comprising the fragment of a full-length antibody, which maintains the ability to specifically bind to the same antigen to which the full-length antibody binds, and/or competes with the full-length antibody for the specific binding to the antigen. See generally, *Fundamental Immunology*, Ch. 7 (Paul, W., ed., 2nd edition, Raven Press, N.Y. (1989), which is incorporated herein by reference in its entirety for all purposes. The antigen-binding fragment of the antibody can be produced by recombinant DNA technology or by enzymatic or chemical cleavage of an intact antibody. In some cases, the antigen-binding fragment includes Fab, Fab', F(ab')$_2$, Fd, Fv, dAb, and complementarity determining region (CDR) fragments, single chain antibody fragments (e.g., scFv), chimeric antibodies, diabodies, and polypeptides comprising at least a portion of the antibody sufficient to impart specific antigen binding ability to them.

As used herein, the term "Fd fragment" refers to an antibody fragment consisting of $V_H$ and CHI domains; the term "Fv fragment" refers to an antibody fragment consisting of the $V_L$ and $V_H$ domains of a single arm of an antibody; the term "dAb fragment" refers to an antibody fragment consisting of a $V_H$ domain (Ward et al., *Nature* 341:544-546 (1989)); the term "Fab fragment" refers to an antibody fragment consisting of $V_L$, $V_H$, $C_L$, and $C_H1$ domains; and the term "F(ab')$_2$ fragment" refers to an antibody fragment comprising two Fab fragments linked by the disulfide bridge on a hinge region.

In some cases, the antigen-binding fragment of the antibody is a single chain antibody (e.g., scFv) in which the $V_L$ and $V_H$ domains are paired to form a monovalent molecule via a linker that enables them to produce a single polypeptide chain (see, e.g., Bird et al., *Science* 242:423-426 (1988) and Huston et al., *Proc. Natl. Acad. Sci. USA* 85:5879-5883 (1988)). Such scFv molecules may have a general structure: NH$_2$-$V_L$-linker-$V_H$-COOH or NH$_2$-$V_H$-linker-$V_L$-COOH. An appropriate linker in prior art consists of GGGGS amino acid sequence repeats or a variant thereof. For example, a linker having the amino acid sequence (GGGGS)$_4$ can be used, but variants thereof can also be used (Holliger et al. (1993), *Proc. Natl. Acad. Sci. USA* 90: 6444-6448). Other linkers that can be used in the present invention are described by Alfthan et al. (1995), *Protein Eng.* 8:725-731; Choi et al. (2001), *Eur. J. Immunol.* 31: 94-106; Hu et al. (1996), *Cancer Res.* 56:3055-3061; Kipriyanov et al. (1999), *J. Mol. Biol.* 293:41-56; and Roovers et al. (2001), *Cancer Immunol.*

In some cases, the antigen-binding fragment of the antibody is a diabody, that is, a bivalent antibody, in which the $V_H$ and $V_L$ domains are expressed on a single polypeptide chain. However, the linker used is too short to allow the pairing of the two domains on one chain, thereby the domains are forced to pair with the complementary domains on another chain and two antigen-binding sites are generated (see, e.g., Holliger P. et al., *Proc. Natl. Acad. Sci. USA* 90:6444-6448 (1993), and Poljak R. J. et al., *Structure* 2: 1121-1123 (1994)).

In other cases, the antigen-binding fragment of the antibody is a "bispecific antibody", which refers to a conjugate formed from a primary antibody (fragment) and a secondary antibody (fragment) or antibody analog via a linker; the methods of conjugation include, but are not limited to, chemical reaction, gene fusion, and enzyme catalysis. The antigen-binding fragment of the antibody may be a "multispecific antibody" including, for example, a trispecific antibody and a tetraspecific antibody, the former being an antibody with three different kinds of antigen-binding specificity, and the latter being an antibody with four different kinds of antigen-binding specificity. For example, a designed ankyrin repeat protein (DARPin) is linked to an IgG antibody, a scFv-Fc antibody fragment or combinations thereof, such as CN104341529A. An anti-IL-17a fynomer binds to an anti-IL-6R antibody, such as WO2015141862A1.

Antigen-binding fragments of antibodies (e.g., the antibody fragments described above) can be obtained from a given antibody (e.g., monoclonal antibody 26B12H1L1, 26B12H4L1, 26B12H2L2, 26B12H3L2, 26B12H2L3, 26B12H3L3, 26B12H1L4 or 26B12H4L4 provided in the present invention) using conventional techniques known to those skilled in the art (e.g., recombinant DNA technology or enzymatic or chemical cleavage), and the antigen-binding fragments of antibodies are screened for specificity in the same manner as for intact antibodies.

As used herein, the terms "mAb" and "monoclonal antibody" refer to an antibody or a fragment of an antibody that is derived from a group of highly homologous antibodies, i.e., from a group of identical antibody molecules, except for natural mutations that may occur spontaneously. The monoclonal antibody is highly specific for a single epitope on an antigen. The polyclonal antibody, relative to the monoclonal antibody, generally comprises at least 2 or more different antibodies which generally recognize different epitopes on an antigen. Monoclonal antibodies can generally be obtained using hybridoma technology first reported by Kohler et al. (Köhler G, Milstein C. Continuous cultures of fused cells secreting antibody of predefined specificity [J]. *Nature,* 1975; 256(5517): 495), but can also be obtained using recombinant DNA technology (see, e.g., U.S. Pat. No. 4,816,567).

As used herein, the term "humanized antibody" refers to an antibody or antibody fragment obtained when all or a part of CDRs of a human immunoglobulin (receptor antibody) are replaced by the CDRs of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, e.g., Jones et al., *Nature* 1986; 321: 522-525; Reichmann et al., *Nature* 1988; 332:323-329; Presta, *Curr. Op. Struct. Biol.,* 1992; 2:593-596; and Clark M. Antibody humanization: a case of the 'Emperor's new clothes'? [J]. *Immunol. Today,* 2000; 21(8): 397-402.

As used herein, the term "isolated" refers to obtaining by artificial means from a natural state. If a certain "isolated" substance or component is present in nature, it may be the case that a change occurs in its natural environment, or that it is isolated from the natural environment, or both. For example, a certain non-isolated polynucleotide or polypeptide naturally occurs in a certain living animal, and the same polynucleotide or polypeptide with high purity isolated from such a natural state is referred to as an isolated polynucleotide or polypeptide.

The term "isolated" does not exclude the existence of artificial or synthetic substances or other impurities that do not affect the activity of the substance.

As used herein, the term "vector" refers to a nucleic acid vehicle into which a polynucleotide can be inserted. When a vector allows the expression of the protein encoded by the inserted polynucleotide, the vector is referred to as an expression vector. The vector can be introduced into a host cell by transformation, transduction or transfection, such that the genetic substance elements carried by the vector can be expressed in the host cell. Vectors are well known to those skilled in the art, including but not limited to: plasmids; phagemids; cosmids; artificial chromosomes, such as yeast artificial chromosome (YAC), bacterial artificial chromosome (BAC), or P1-derived artificial chromosome (PAC); phages such as lambda phages or M13 phages; and animal viruses. Animal viruses that can be used as vectors include, but are not limited to retroviruses (including lentiviruses), adenoviruses, adeno-associated viruses, herpes viruses (such as herpes simplex virus), poxviruses, baculoviruses, papillomaviruses, and papovaviruses (such as SV40). A vector may comprise a variety of elements that control expression, including, but not limited to, promoter sequences, transcription initiation sequences, enhancer sequences, selection elements and reporter genes. In addition, the vector may further comprise a replication initiation site.

As used herein, the term "host cell" refers to cells to which vectors can be introduced, including, but not limited to, prokaryotic cells such as *E. coli* or *Bacillus subtilis,* fungal cells such as yeast cells or *aspergillus,* insect cells such as S2 *drosophila* cells or Sf9, or animal cells such as fibroblasts, CHO cells, COS cells, NSO cells, HeLa cells, GS cells, BHK cells, HEK 293 cells, or human cells.

As used herein, the term "specific binding" refers to a non-random binding reaction between two molecules, such as a reaction between an antibody and an antigen it targets. In some embodiments, an antibody specifically binding to an antigen (or an antibody specific to an antigen) means that the antibody binds to the antigen with an affinity ($K_D$) of less than about $10^{-5}$ M, e.g., less than about $10^{-6}$ M, $10^{-7}$ M, $10^{-8}$ M, $10^{-9}$ M or $10^{-10}$ M or less.

As used herein, the term "$K_D$" refers to a dissociation equilibrium constant for a specific antibody-antigen interaction, which is used to describe the binding affinity between the antibody and the antigen. A smaller dissociation equilibrium constant indicates a stronger antibody-antigen binding and a higher affinity between the antibody and the antigen. Generally, the antibodies bind to antigens (e.g., TIGIT protein) with a dissociation equilibrium constant ($K_D$) of less than about $10^{-5}$ M, e.g., less than about $10^{-6}$ M, $10^{-7}$ M, $10^{-8}$ M, $10^{-9}$ M or $10^{-10}$ M or less. $K_D$ can be determined using methods known to those skilled in the art, e.g., using a Fortebio system.

As used herein, the terms "monoclonal antibody" and "mAb" have the same meaning and are used interchangeably; the terms "polyclonal antibody" and "pAb" have the same meaning and are used interchangeably; the terms "polypeptide" and "protein" have the same meaning and are used interchangeably. Besides, as used herein, amino acids are generally represented by single-letter and three-letter abbreviations known in the art. For example, alanine can be represented by A or Ala.

As used herein, the term "pharmaceutically acceptable carrier and/or excipient" refers to a carrier and/or excipient that is pharmacologically and/or physiologically compatible with the subject and the active ingredient. Such carriers and/or excipients are well known in the art (see, e.g., *Remington's Pharmaceutical Sciences,* edited by Gennaro A R, 19*th* Ed., Pennsylvania, Mack Publishing Company, 1995), including but not limited to: pH regulators, surfactants, adjuvants and ionic strength enhancers. For example, the pH regulators include, but are not limited to, phosphate buffer; the surfactants include, but are not limited to, cationic, anionic or non-ionic surfactants, such as Tween-80; the ionic strength enhancers include, but are not limited to, sodium chloride.

As used herein, the term "effective amount" refers to an amount sufficient to obtain or at least partially obtain a desired effect. For example, a prophylactically effective amount against a disease (e.g., a tumor) refers to an amount sufficient to prevent, stop, or delay the onset of the disease (e.g., a tumor); a therapeutically effective amount refers to an amount sufficient to cure or at least partially stop diseases and complications thereof in patients suffering from the disease.

As used herein, when referring to the amino acid sequence of TIGIT protein (NCBI GenBank: NP_776160.2), it includes the full length of the TIGIT protein, or the extracellular fragment TIGIT ECD of TIGIT or a fragment comprising TIGIT ECD; also included are fusion proteins of the full length of the TIGIT protein or fusion proteins of TIGIT ECD, such as a fragment fused to an Fc protein fragment of a mouse or human IgG (mFc or hFc). However, those skilled in the art will appreciate that in the amino acid sequence of the TIGIT protein, mutations or variations (including but not limited to, substitutions, deletions and/or additions) may naturally occur or can be artificially introduced without affecting biological functions thereof. Therefore, in the present invention, the term "TIGIT protein" should include all such sequences, including their natural or artificial variants. In addition, when describing a sequence fragment of the TIGIT protein, it also includes the corresponding sequence fragments in their natural or artificial variants.

As used herein, the terms "hybridoma" and "hybridoma cell line" are used interchangeably, and when referring to the terms "hybridoma" and "hybridoma cell line", they also include subclones and progeny cells of the hybridoma.

In the present invention, the terms "first" (e.g., first product) and "second" (e.g., second product) are used for distinguishing or clarity in expression and do not carry typical sequential meanings, unless otherwise specified.

Beneficial Effects of the Present Invention

The monoclonal antibodies of the present invention can specifically bind to TIGIT very well and have strong affinity. They reduce the inhibitory effect of TIGIT on immune cells, promote the activity of T cells, reverse NK cell exhaustion, and enhance the killing effect of immune cells on tumors. They can be used for preparing a medicament for inhibiting TIGIT and treating or preventing diseases such as tumors (e.g., liver cancer, kidney cancer, brain tumor, urothelial carcinoma, bone tumor, cholangiocarcinoma, non-small cell lung cancer, small cell lung cancer, breast cancer, ovarian cancer, colorectal cancer, melanoma, pancreatic cancer, cervical tumor, multiple myeloma, Hodgkin's lymphoma, non-Hodgkin's lymphoma, B-lymphoma, ovarian cancer, plasma cell cancer, endometrial cancer, prostate cancer, and testicular cancer), thus having prospect for application and marketing.

DEPOSITED BIOLOGICAL MATERIAL

Figure 1:
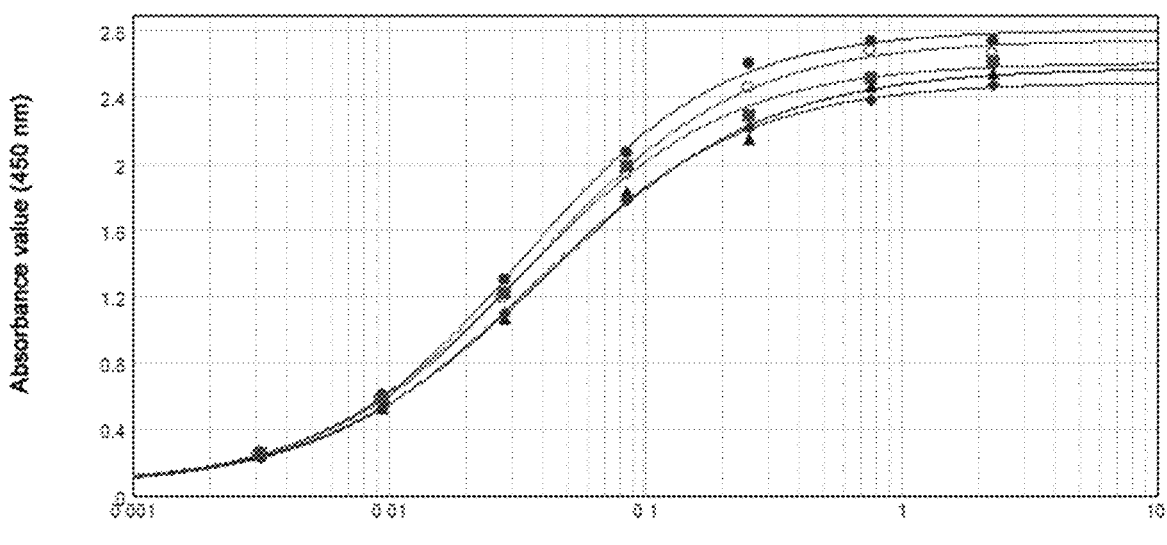
FIG. 1: the results of assays for the activity of antibodies 26B12H1L1, 26B12H2L2, 26B12H2L3 and 26B12H3L2 binding to TIGIT-mFc.

Hybridoma cell line LT019 was deposited at China Center for Type Culture Collection (CCTCC) on Oct. 23, 2020, and accepted, under CCTCC NO. C2020208, the depository address being Wuhan University, Wuhan, China, postal code: 430072.

The present invention relates to the following sequences 1 to 26:

1. The amino acid sequence of 26B12VH (SEQ ID NO: 1)

EVQLQESGPGLVKPSQSLSLTCTVT<u>GHSFTSDYAWN</u>WIRQFPGNR

LEWMGY<u>ISYSDSTNYNPSLKSR</u>ISITRDTSKNQFFLQMNSVTTEDT

ATYYC<u>ARLDYGNYGGAMDY</u>WGQGTSVTVSS

2. The nucleotide sequence of 26B12VH (SEQ ID NO: 2)

GAGGTGCAGCTGCAGGAGTCTGGACCTGGCCTGGTGAAACCC

TCTCAGTCTCTGTCCCTCACCTGCACTGTCACT<u>GGCCACTCAT

TCACCAGTGATTATGCCTGGAACTGGATCCGGCAGTTTCCAGG

AAACAGACTGGAGTGGATGGGCTAC</u>ATAAGCTACAGTGATAG

<u>CACTAACTACAACCCATCTCTCAAAAGTCGAATCTCTATCACT

CGAGACACATCCAAGAACCAGTTCTTCTTGCAGATGAATTCTG

-continued

TGACTACTGAGGACACAGCCACATATTACTGTGCAAGATTGGA

CTATGGTAACTACGGTGGGGCTATGGACTACTGGGGTCAAGG

GACCTCAGTCACCGTCTCCTCA

3. HCDR1:
                                        (SEQ ID NO: 3)
GHSFTSDYA

4. HCDR2:
                                        (SEQ ID NO: 4)
ISYSDST

5. HCDR3:
                                        (SEQ ID NO: 5)
ARLDYGNYGGAMDY

6. The amino acid sequence of 26B12VL
                                        (SEQ ID NO: 6)
DIVLTQSHEFMSTSLRDRVSITCKSSQHVSTAVAWYQQKPGQSPK

LLIYSASYRYTGVPDRFTGSGSGTDFTFTISSVKAEDLAVYYCQQH

YITPWTFGGGTKLEIK

7. The nucleotide sequence of 26B12VL
                                        (SEQ ID NO: 7)
GATATTGTGCTAACTCAGTCTCACGAATTCATGTCCACCTCAT

TACGAGACAGGGTCAGCATCACCTGCAAATCCAGTCAACATGT

GAGTACTGCTGTAGCCTGGTATCAACAGAAACCAGGACAATCT

CCTAAACTACTGATTTACTCGGCATCCTACCGGTACACTGGAG

TCCCTGATCGCTTCACTGGCAGTGGATCTGGGACGGATTTCAC

TTTCACCATCAGCAGTGTGAAGGCTGAAGACCTGGCAGTTTAT

TACTGTCAGCAACATTATATTACTCCGTGGACGTTCGGTGGAG

GCACCAAGCTGGAAATAAAA

8. LCDR1:
                                        (SEQ ID NO: 8)
QHVSTA

9. LCDR2:
                                        (SEQ ID NO: 9)
SAS

10. LCDR3:
                                        (SEQ ID NO: 10)
QQHYITPWT

11. The amino acid sequence of 26B12H1
                                        (SEQ ID NO: 11)
DVQLQESGPGLVKPSQTLSLTCTVSGHSFTSDYAWNWIRQFPGK

GLEWIGYISYSDSTNYNPSLKSRITISRDTSKNQFFLQLNSVTAADT

ATYYCARLDYGNYGGAMDYWGQGTSVTVSS

12. The nucleotide sequence of 26B12H1
                                        (SEQ ID NO: 12)
GATGTGCAGCTGCAGGAGAGCGGCCCCGGACTGGTGAAGCCT

TCCCAGACCCTGTCTCTGACCTGTACAGTGTCTGGCCACAGCT

TCACATCCGACTACGCCTGGAACTGGATCAGGCAGTTTCCAGG

CAAGGGCCTGGAGTGGATCGGCTACATCTCTTATAGCGACTCC

ACCAACTATAATCCCTCTCTGAAGAGCCGGATCACCATCAGCA

GAGATACATCCAAGAACCAGTTCTTTCTGCAGCTGAACAGCGT

GACAGCCGCCGACACCGCCACATACTATTGCGCCCGGCTGGA

CTACGGCAATTATGGCGGAGCCATGGATTACTGGGGCCAGGG

CACCTCCGTGACAGTGAGCTCC

13. The amino acid sequence of 26B12H2
                                        (SEQ ID NO: 13)
DVQLQESGPGLVKPSQTLSLTCTVSGHSFTSDYAWSWIRQPPGKG

LEWIGYISYSDSTNYNPSLKSRVTISRDTSKNQFSLKLSSVTAADTA

VYYCARLDYGNYGGAMDYWGQGTSVTVSS

14. The nucleotide sequence of 26B12H2
                                        (SEQ ID NO: 14)
GATGTGCAGCTGCAGGAGTCTGGCCCAGGACTGGTGAAGCCA

AGCCAGACCCTGTCCCTGACCTGTACAGTGTCCGGCCACTCTT

TTACAAGCGACTACGCCTGGTCTTGGATCAGGCAGCCCCCTG

GCAAGGGACTGGAGTGGATCGGCTACATCTCCTATTCTGACA

GCACCAACTATAATCCCTCCCTGAAGTCTCGGGTGACCATCTC

TAGAGATACAAGCAAGAACCAGTTCTCCCTGAAGCTGAGCTCC

GTGACCGCAGCAGACACAGCCGTGTACTATTGCGCCCGGCTG

GACTACGGCAATTATGGCGGAGCCATGGATTACTGGGGCCAG

GGCACCAGCGTGACAGTGTCTAGC

15. The amino acid sequence of 26B12H3
                                        (SEQ ID NO: 15)
DVQLQESGPGLVKPSQTLSLTCTVSGHSFTSDYAWSWIRQPPGKG

LEWIGYISYSDSTNYNPSLKSRVTISVDTSKNQFSLKLSSVTAADTA

VYYCARLDYGNYGGAMDYWGQGTSVTVSS

16. The nucleotide sequence of 26B12H3
                                        (SEQ ID NO: 16)
GATGTGCAGCTGCAGGAGTCTGGCCCAGGACTGGTGAAGCCA

AGCCAGACCCTGTCCCTGACCTGTACAGTGTCCGGCCACTCTT

TTACAAGCGACTACGCCTGGTCTTGGATCAGACAGCCCCCTGG

CAAGGGACTGGAGTGGATCGGCTACATCTCCTATTCTGACAGC

ACCAACTATAATCCCTCCCTGAAGTCTAGAGTGACCATCTCTG

TGGATACAAGCAAGAACCAGTTCTCCCTGAAGCTGAGCTCCGT

GACCGCAGCAGACACAGCCGTGTACTATTGCGCCCGGCTGGA

CTACGGCAATTATGGCGGAGCCATGGATTACTGGGGCCAGGG

CACCAGCGTGACAGTGTCTAGC

17. The amino acid sequence of 26B12H4
                                        (SEQ ID NO: 17)
DVQLQESGPGLVKPSQTLSLTCTVSGHSFTSDYAWNWIRQFPGK

GLEWMGYISYSDSTNYNPSLKSRITISRDTSKNQFFLQLNSVTAAD

TATYYCARLDYGNYGGAMDYWGQGTSVTVSS

18. The nucleotide sequence of 26B12H4
                                        (SEQ ID NO: 18)
GATGTGCAGCTGCAGGAGAGCGGCCCCGGACTGGTGAAGCCT

TCCCAGACCCTGTCTCTGACCTGTACAGTGTCTGGCCACAGCT

TCACATCCGACTACGCCTGGAACTGGATCAGGCAGTTTCCAGG

CAAGGGCCTGGAGTGGATGGGCTACATCTCTTATAGCGACTC

CACCAACTATAATCCCTCTCTGAAGAGCCGGATCACCATCAGC

AGAGATACATCCAAGAACCAGTTCTTTCTGCAGCTGAACAGCG

-continued

TGACAGCCGCCGACACCGCCACATACTATTGCGCCCGGCTGG

ACTACGGCAATTATGGCGGAGCCATGGATTACTGGGGCCAGG

GCACCTCCGTGACAGTGAGCTCC

19. The amino acid sequence of 26B12L1

(SEQ ID NO: 19)

DIQMTQSPKSLSTSVGDRVTITCRSSQHVSTAVAWYQQKPGKSPK

LLIYSASYRYSGVPDRFSGSGSGTDFTFTISSVQPEDFATYYCQQH

YITPWTFGGGTKLEIK

20. The nucleotide sequence of 26B12L1

(SEQ ID NO: 20)

GACATCCAGATGACCCAGTCCCCTAAGTCCCTGTCTACAAGCG

TGGGCGATCGGGTGACCATCACATGTAGAAGCTCCCAGCACG

TGTCTACCGCAGTGGCATGGTACCAGCAGAAGCCAGGCAAGA

GCCCTAAGCTGCTGATCTATTCCGCCTCTTACAGGTATTCCGG

AGTGCCAGACCGGTTTAGCGGCTCCGGCTCTGGCACCGATTT

CACCTTTACAATCTCTAGCGTGCAGCCAGAGGACTTCGCCACA

TACTATTGCCAGCAGCACTACATCACCCCATGGACCTTCGGCG

GCGGCACAAAGCTGGAGATCAAG

21. The amino acid sequence of 26B12L2

(SEQ ID NO: 21)

DIQMTQSPSSLSASVGDRVTITCRSSQHVSTALAWYQQKPGKSPK

LLIYSASSRYSGVPDRESGSGSGTDFTFTISSLQPEDFATYYCQQHY

ITPWTFGGGTKLEIK

22. The nucleotide sequence of 26B12L2

(SEQ ID NO: 22)

GACATCCAGATGACCCAGTCCCCTAGCTCCCTGTCTGCCAGCG

TGGGCGATAGGGTGACCATCACATGTAGATCTAGCCAGCACG

TGTCTACAGCCCTGGCATGGTACCAGCAGAAGCCAGGCAAGA

GCCCTAAGCTGCTGATCTACTCCGCCTCCTCTAGGTATTCTGG

AGTGCCAGACCGGTTTTCCGGCTCTGGCAGCGGCACCGATTT

CACCTTTACAATCAGCTCCCTGCAGCCAGAGGACTTCGCCACA

TACTATTGCCAGCAGCACTATATCACCCCATGGACCTTCGGCG

GCGGCACCAAGCTGGAGATCAAG

23. The amino acid sequence of 26B12L3

(SEQ ID NO: 23)

DIQMTQSPSSLSASVGDRVTITCRASQHVSTALAWYQQKPGKAPK

LLIYSASSLQSGVPSRFSGSGSGTDFTLTISSLQPEDFATYYCQQHY

ITPWTFGGGTKLEIK

24. The nucleotide sequence of 26B12L3

(SEQ ID NO: 24)

GACATCCAGATGACCCAGTCCCCTAGCTCCCTGAGCGCCTCCG

TGGGCGATAGGGTGACCATCACATGTAGAGCCTCTCAGCACG

TGAGCACAGCCCTGGCATGGTACCAGCAGAAGCCAGGCAAGG

CCCCTAAGCTGCTGATCTATAGCGCCTCTAGCCTGCAGTCCGG

AGTGCCATCTCGGTTCTCTGGCAGCGGCTCCGGAACCGACTTT

ACCCTGACAATCTCCTCTCTGCAGCCAGAGGATTTCGCCACAT

-continued

ACTATTGCCAGCAGCACTACATCACCCCATGGACCTTCGGCGG

CGGCACCAAGCTGGAGATCAAG

25. The amino acid sequence of 26B12L4

(SEQ ID NO: 25)

DIQMTQSPKSMSTSVGDRVTITCRSSQHVSTAVAWYQQKPGKSP

KLLIYSASYRYSGVPDRFSGSGSGTDFTFTISSVQPEDFATYYCQQ

HYITPWTFGGGTKLEIK

26. The nucleotide sequence of 26B12L4

(SEQ ID NO: 26)

GACATCCAGATGACCCAGTCCCCTAAGTCCATGTCTACAAGCG

TGGGCGACAGGGTGACCATCACATGTAGAAGCTCCCAGCACG

TGTCTACCGCAGTGGCATGGTACCAGCAGAAGCCAGGCAAGA

GCCCTAAGCTGCTGATCTATTCCGCCTCTTACAGGTATTCCGG

AGTGCCAGACCGGTTTAGCGGCTCCGGCTCTGGCACCGATTT

CACCTTTACAATCTCTAGCGTGCAGCCAGAGGACTTCGCCACA

TACTATTGCCAGCAGCACTACATCACCCCATGGACCTTCGGCG

GCGGCACAAAGCTGGAGATCAAG

DETAILED DESCRIPTION

The embodiments of the present invention will be described in detail below with reference to the examples. Those skilled in the art will appreciate that the following examples are only for illustrating the present invention, and should not be construed as limitations to the scope of the present invention. Examples where the specific technologies or conditions are not specified are performed according to the technologies or conditions described in the publications of the art (e.g., see, *Molecular Cloning: A Laboratory Manual*, authored by J. Sambrook et al., and translated by Huang Peitang et al., third edition, Science Press) or according to the product manual. Reagents or instruments used are commercially available conventional products if the manufacturers thereof are not specified. For example, 293T can be purchased from ATCC.

In the following examples of the present invention, BALB/c mice used were purchased from Guangdong Medical Laboratory Animal Center. In the following examples of the present invention, the sequence 34 and the sequence 36 in the Chinese Publication Patent CN108290946A can be referred to for the sequence of the positive control antibody RG6058 used.

In the following examples of the present invention, the cell line 293T-TIGIT used was constructed by Akeso Biopharma Co. Ltd. The cell line 293T-TIGIT was prepared by viral transfection of HEK293T cells using 3rd Generation Lentiviral Systems (see, e.g., A Third Generation Lentivirus Vector with a Conditional Packaging System. Dull T, Zufferey R, Kelly M, Mandel R J, Nguyen M, Trono D, and Naldini L., *J Virol.*, 1998. 72(11):8463-8471), wherein the lentivirus expression vector used was pCDH-CMV-PD-1FL-Puro (TIGIT, Genebank ID: NP_776160.2; vector pCDH-CMV-Puro, purchased from Youbio, Cat. No. VT1480).

Example 1: Preparation of Anti-TIGIT Antibody 26B12

1. Preparation of Hybridoma Cell Line LT019

The antigen used for preparing the anti-TIGIT antibody was human TIGIT-mFc (TIGIT was GenbankID: NP_776160.2). Spleen cells of immunized mice were fused with myeloma cells of the mice to prepare hybridoma cells. With human TIGIT-mFc taken as antigens, the hybridoma cells were screened by indirect ELISA to obtain hybridoma cells capable of secreting antibodies specifically binding to TIGIT. The hybridoma cells obtained by screening were subjected to limiting dilution to obtain a stable hybridoma cell line. The above hybridoma cell line was designated hybridoma cell line LT019, and the monoclonal antibody secreted by the cell line was designated 26B12.

Hybridoma cell line LT019 was deposited at China Center for Type Culture Collection (CCTCC) on Oct. 23, 2020 under CCTCC NO. C2020208, the depository address being Wuhan University, Wuhan, China, postal code: 430072.

2. Preparation of Anti-TIGIT Antibody 26B12

The LT019 cell line prepared above was cultured with a chemical defined medium (CD medium, containing 1% penicillin-streptomycin) at 37° C./5% $CO_2$. After 7 days, the cell culture supernatant was collected, subjected to high-speed centrifugation and vacuum filtration through a micro-filtration membrane, and purified by using a HiTrap protein A HP column to obtain antibody 26B12.

Example 2: Sequence Analysis of Anti-TIGIT Antibody 26B12 mRNA was extracted from the cell line LT019 cultured in Example 1 according to the method described in the manual of RNAprep pure Cell/Bacteria Kit (Tiangen, Cat. No. DP430).

cDNA was synthesized according to the manual of Invitrogen SuperScript® III First-Strand Synthesis System for RT-PCR and amplified by PCR.

The PCR amplification products were directly subjected to TA cloning according to the manual of the pEASY-T1 Cloning Kit (Transgen CT101).

The TA cloning products were directly sequenced, and the sequencing results are as follows:

The nucleotide sequence of the heavy chain variable region is set forth in SEQ ID NO: 2 with a length of 363 bp.

The encoded amino acid sequence is set forth in SEQ ID NO: 1 with a length of 121 amino acids, wherein the sequences of heavy chain HCDR1, HCDR2 and HCDR3 are set forth in SEQ ID NOs: 3, 4 and 5, respectively.

The nucleotide sequence of the light chain variable region is set forth in SEQ ID NO: 7 with a length of 321 bp.

The encoded amino acid sequence is set forth in SEQ ID NO: 6 with a length of 107 amino acids, wherein the sequences of light chain LCDR1, LCDR2 and LCDR3 are set forth in SEQ ID NOs: 8, 9 and 10, respectively.

Example 3: Design and Preparation of Light and Heavy Chains of Humanized Anti-Human TIGIT Antibodies

1. Design of Light and Heavy Chains of Humanized Anti-Human TIGIT Antibodies 26B12H1L1, 26B12H4L1, 26B12H2L2, 26B12H3L2, 26B12H2L3, 26B12H3L3, 26B12H1L4 and 26B12H4L4

Based on the three-dimensional crystal structure of human TIGIT protein and the sequence of antibody 26B12 obtained in Example 2, the antibody model was simulated by computer, and mutations were designed according to the model to obtain the variable region sequences of antibodies 26B12H1L1, 26B12H4L1, 26B12H2L2, 26B12H3L2, 26B12H2L3, 26B12H3L3, 26B12H1L4 and 26B12H4L4 (antibody constant region sequences from the NCBI database: the heavy chain constant region is Ig gamma-1 chain C region, ACCESSION: P01857; the light chain constant region is Ig kappa chain C region, ACCESSION: P01834).

The designed variable region sequences are shown in Table A below.

| No. | Name | Amino acid sequence of heavy chain variable region SEQ ID NO: | Nucleotide sequence of heavy chain variable region SEQ ID NO: | Amino acid sequence of light chain variable region SEQ ID NO: | Nucleotide sequence of light chain variable region SEQ ID NO: |
|---|---|---|---|---|---|
| 1 | 26B12H1L1 | 11 | 12 | 19 | 20 |
| 2 | 26B12H4L1 | 17 | 18 | 19 | 20 |
| 3 | 26B12H2L2 | 13 | 14 | 21 | 22 |
| 4 | 26B12H2L3 | 13 | 14 | 23 | 24 |
| 5 | 26B12H3L2 | 15 | 16 | 21 | 22 |
| 6 | 26B12H3L3 | 15 | 16 | 23 | 24 |
| 7 | 26B12H1L4 | 11 | 12 | 25 | 26 |
| 8 | 26B12H4L4 | 17 | 18 | 25 | 26 |

For the above 8 antibodies 26B12H1L1, 26B12H4L1, 26B12H2L2, 26B12H3L2, 26B12H2L3, 26B12H3L3, 26B12H1L4 and 26B12H4L4, the length of the nucleotide sequences of the heavy chain variable regions was 363 bp, and the length of the encoded amino acid sequences was 121 aa; the length of the nucleotide sequences of the light chain variable regions was 321 bp, and the length of the encoded amino acid sequences was 107 aa.

Moreover, the above 8 antibodies had the same HCDR1-HCDR3 and LCDR1-LCDR3:

the sequences of the HCDR1, HCDR2 and HCDR3 are set forth in SEQ ID NOs: 3, 4 and 5, respectively; and the sequences of the LCDR1, LCDR2 and LCDR3 are set forth in SEQ ID NOs: 8, 9 and 10, respectively.

2. Preparation of Humanized Antibodies 26B12H1L1, 26B12H4L1, 26B12H2L2, 26B12H3L2, 26B12H2L3, 26B12H3L3, 26B12H1L4 and 26B12H4L4

The heavy chain constant regions were all Ig gamma-1 chain C region, ACCESSION: P01857; the light chain constant regions were all Ig kappa chain C region, ACCESSION: P01834.

Heavy chain cDNA and light chain cDNA of 26B12H1L1, heavy chain cDNA and light chain cDNA of 26B12H4L1, heavy chain cDNA and light chain cDNA of 26B12H2L2, heavy chain cDNA and light chain cDNA of 26B12H3L2, heavy chain cDNA and light chain cDNA of 26B12H2L3, heavy chain cDNA and light chain cDNA of 26B12H3L3, heavy chain cDNA and light chain cDNA of 26B12H1L4, heavy chain cDNA and light chain cDNA of 26B12H2L4, and heavy chain cDNA and light chain cDNA of 26B12H4L4 were separately cloned into pUC57simple (provided by Genscript) vectors to obtain pUC57simple-26B12H1, pUC57simple-26B12L1; pUC57simple-26B12H4, pUC57simple-26B12L1; pUC57simple-26B12H2, pUC57simple-26B12L2; pUC57simple-26B12H3, pUC57simple-26B12L2; pUC57simple-26B12H2, pUC57simple-26B12L3; pUC57simple-26B12H3, pUC57simple-26B12L3; pUC57simple-26B12H1, pUC57simple-26B12L4; pUC57simple-26B12H2, pUC57simple-26B12L4; and pUC57simple-26B12H4, pUC57simple-26B12L4, respectively. With reference to the standard techniques described in *Molecular Cloning: A Laboratory Manual* (Second Edition), the heavy and light chain full-length genes synthesized by EcoRI&HindIII digestion were subcloned into expression vector pcDNA3.1 by digestion with restriction enzyme EcoRI&HindIII to obtain expression plasmids pcDNA3.1-26B12H1, pcDNA3.1-26B12L1, pcDNA3.1-26B12H4, pcDNA3.1-126B12H2, pcDNA3.1-26B12L2, pcDNA3.1-26B12H3, pcDNA3.1-26B12L3 and pcDNA3.1-26B12L4, and the heavy/light chain genes of the recombinant expression plasmids were further sequenced. Then the designed gene combinations comprising corresponding light and heavy chain recombinant plasmids (pcDNA3.1-26B12H1/pcDNA3.1-26B12L1, pcDNA3.1-26B12H4/pcDNA3.1-26B12L1, pcDNA3.1-26B12H2/pcDNA3.1-26B12L2, pcDNA3.1-26B12H3/pcDNA3.1-26B12L2, pcDNA3.1-26B12H2/pcDNA3.1-26B12L3, pcDNA3.1-26B12H3/pcDNA3.1-26B12L3, pcDNA3.1-26B12H1/pcDNA3.1-26B12L4 and pcDNA3.1-26B12H4/pcDNA3.1-26B12L4) were separately co-transfected into 293F cells, and the cultures were collected and purified. After the sequences were verified, endotoxin-free expression plasmids were prepared, and were transiently transfected into HEK293 cells for antibody expression. After 7 days of culture, the cell cultures were collected and subjected to affinity purification on a Protein A column to obtain humanized antibodies.

Example 4: ELISA Assays for Activity of Antibodies Binding to Antigen TIGIT-mFc Experimental steps: a microplate was coated with goat anti-mouse IgG Fc at 2 μg/mL, and incubated at 4° C. for 16 h. After incubation, the microplate coated with goat anti-mouse IgG Fc was washed once with PBST, and then blocked with a PBST solution containing 1% BSA as a microplate blocking solution for 2 h. After blocking, the microplate was washed 3 times with PBST. Then, 1 μg/mL antigen human TIGIT-mFc was added, and the plate was incubated at 37° C. for 30 min and then washed 3 times with PBST. The antibodies serially diluted with the PBST solution were added to the wells of the microplate. The antibody dilution gradients are shown in Table 1 and Table 2. The microplate containing the test antibodies was incubated at 37° C. for 30 min, and then washed 3 times with PBST. After washing, HRP-labeled goat anti-human IgG Fc secondary antibody working solution diluted in a ratio of 1:5000 was added, and the microplate was incubated at 37° C. for 30 min. After incubation, the plate was washed 4 times with PBST, TMB (Neogen, 308177) was added for chromogenesis in the dark for 4 min, and then a stop solution was added to terminate the chromogenic reaction. The microplate was put into a microplate reader immediately, and the OD value of each well in the microplate was read at 450 nm. The data were analyzed and processed by SoftMax Pro 6.2.1.

Figure 2:
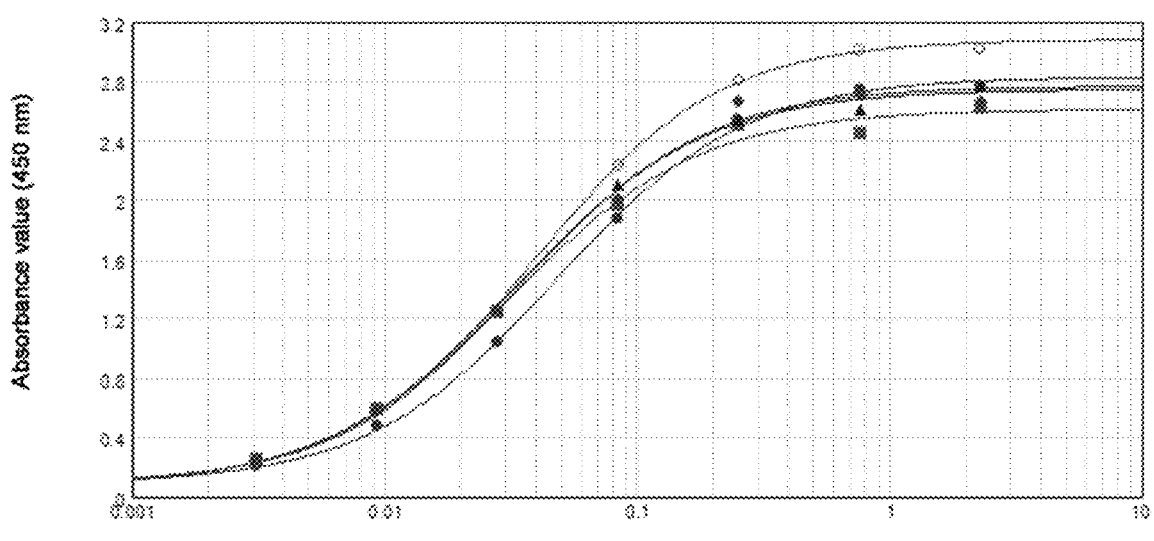
FIG. 2: the results of assays for the activity of antibodies 26B12H3L3, 26B12H1L4, 26B12H4L1 and 26B12H4L4 binding to TIGIT-mFc.

The results of the binding of the antibodies to the antigen TIGIT-mFc are shown in FIGS. 1 and 2. The GD values for all the dosages are shown in Table 1 and Table 2. The $EC_{50}$ of the antibodies binding to the antigen was calculated by curve fitting using antibody concentration as the abscissa and absorbance value as the ordinate, and the results are shown in Table 1 and Table 2, and FIG. 1 and FIG. 2.

TABLE 1

| The results of assays for the activity of 26B12H1L1, 26B12H2L2, 26B12H2L3, 26B12H3L2 and RG6058 binding to TIGIT-mFc |||||||||||
| Coating: goat anti-mouse IgG Fc (2 μg/mL) |||||||||||
| Antibody dilution | TIGIT-mFc (1 μg/mL) ||||||||||
| (μg/mL) | 26B12H1L1 || 26B12H2L2 || 26B12H2L3 || 26B12H3L2 || RG6058 ||
|---|---|---|---|---|---|---|---|---|---|---|
| 0.3330 | 2.789 | 2.701 | 2.623 | 2.609 | 2.560 | 2.542 | 2.513 | 2.430 | 2.644 | 2.689 |
| 0.1110 | 2.722 | 2.771 | 2.460 | 2.572 | 2.413 | 2.528 | 2.368 | 2.394 | 2.516 | 2.863 |
| 0.0370 | 2.539 | 2.676 | 2.322 | 2.253 | 2.162 | 2.137 | 2.142 | 2.292 | 2.332 | 2.605 |
| 0.0123 | 2.001 | 2.126 | 2.001 | 1.965 | 1.853 | 1.811 | 1.706 | 1.861 | 1.855 | 2.028 |
| 0.0041 | 1.262 | 1.349 | 1.211 | 1.221 | 1.038 | 1.103 | 1.106 | 1.092 | 1.142 | 1.263 |
| 0.0014 | 0.593 | 0.613 | 0.542 | 0.627 | 0.506 | 0.544 | 0.546 | 0.527 | 0.569 | 0.602 |
| 0.0005 | 0.264 | 0.265 | 0.249 | 0.258 | 0.237 | 0.243 | 0.224 | 0.229 | 0.238 | 0.254 |
| 0.0000 | 0.056 | 0.051 | 0.053 | 0.046 | 0.052 | 0.049 | 0.049 | 0.050 | 0.053 | 0.049 |
| Secondary antibody | HRP-labeled goat anti-human IgG Fc (1:5000) |||||||||
| $EC_{50}$(nM) | 0.034 || 0.033 || 0.040 || 0.037 || 0.036 ||

TABLE 2

The results of assays for the activity of 26B12H3L3,
26B12H1L4, 26B12H4L1, 26B12H4L4 and RG6058 binding to
TIGIT-mFc
Coating: goat anti-mouse IgG Fc (2 µg/mL)

| Antibody dilution (µg/mL) | TIGIT-mFc (1 µg/mL) | | | | | | | | | |
|---|---|---|---|---|---|---|---|---|---|---|
| | 26B12H3L3 | | 26B12H1L4 | | 26B12H4L1 | | 26B12H4L4 | | RG6058 | |
| 0.3330 | 2.736 | 2.788 | 2.639 | 2.604 | 2.709 | 2.829 | 2.728 | 2.608 | 2.963 | 3.089 |
| 0.1110 | 2.707 | 2.774 | 2.469 | 2.422 | 2.625 | 2.587 | 2.626 | 2.788 | 2.915 | 3.119 |
| 0.0370 | 2.546 | 2.538 | 2.568 | 2.451 | 2.392 | 2.699 | 2.679 | 2.660 | 2.830 | 2.797 |
| 0.0123 | 1.861 | 1.881 | 2.049 | 1.882 | 2.113 | 2.091 | 1.987 | 2.045 | 2.237 | 2.237 |
| 0.0041 | 1.074 | 1.012 | 1.232 | 1.266 | 1.252 | 1.279 | 1.265 | 1.239 | 1.254 | 1.258 |
| 0.0014 | 0.483 | 0.477 | 0.593 | 0.580 | 0.582 | 0.592 | 0.589 | 0.593 | 0.569 | 0.593 |
| 0.0005 | 0.217 | 0.211 | 0.246 | 0.263 | 0.256 | 0.261 | 0.253 | 0.253 | 0.244 | 0.248 |
| 0.0000 | 0.065 | 0.060 | 0.053 | 0.051 | 0.051 | 0.051 | 0.052 | 0.054 | 0.065 | 0.061 |
| Secondary antibody | HRP-labeled goat anti-human IgG Fc (1:5000) | | | | | | | | | |
| $EC_{50}$(nM) | 0.048 | | 0.031 | | 0.033 | | 0.034 | | 0.039 | |

The results show that the antibodies 26B12H1L1, 26B12H4L1, 26B12H2L2, 26B12H3L2, 26B12H2L3, 26B12H3L3, 26B12H1L4 and 26B12H4L4 are all capable of effectively binding to human TIGIT-mFc in a dose-dependent manner, and the binding activities are comparable to that of the positive drug RG6058 for the same target, indicating that the antibodies 26B12H1L1, 26B12H4L1, 26B12H2L2, 26B12H3L2, 26B12H2L3, 26B12H3L3, 26B12H1L4 and 26B12H4L4 have the function of effectively binding to TIGIT.

Example 5: Competitive ELISA Assays for Activity of Antibodies Competing with CD155-hFc-Biotin for Binding to TIGIT-mFc Experimental steps: a microplate was coated with TIGIT-mFc at 2 µg/mL, and incubated at 4° C. overnight. After incubation, the antigen-coated microplate was rinsed once with PBST, and then blocked with a PBST solution containing 1% BSA as a microplate blocking solution for 2 h. After blocking, the microplate was washed 3 times with PBST. The antibodies serially diluted with the PBST solution was added to the microplate. The antibody concentrations are shown in Table 3 and Table 4. After the microplate was incubated at room temperature for 10 min, equal volumes of 2 µg/mL CD155-hFc-Biotin (final concentration: 1 µg/mL) were added, and mixed well with the antibodies. The microplate was incubated at 37° C. for 30 min, and then washed 3 times with PBST. After washing, SA-HRP working solution diluted in a ratio of 1:4000 was added, and the microplate was incubated at 37° C. for 30 min. After incubation, the plate was washed 4 times with PBST, TMB (Neogen, 308177) was added for chromogenesis in the dark for 5 min, and then a stop solution was added to terminate the chromogenic reaction. The microplate was put into a microplate reader immediately, and the OD value of each well in the microplate was read at 450 nm. The data were analyzed and processed by SoftMax Pro 6.2.1.

Figure 3:
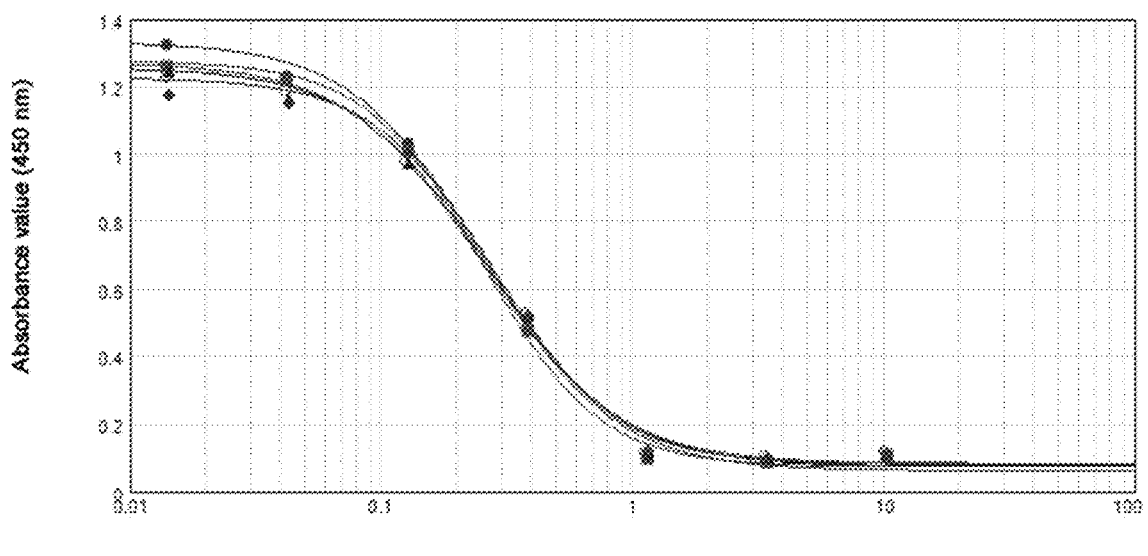
FIG. 3: the results of assays for the activity of antibodies 26B12H1L1, 26B12H2L2, 26B12H2L3 and 26B12H3L2 competing with human CD155-hFc-Biotin for binding to TIGIT-mFc.
Figure 4:
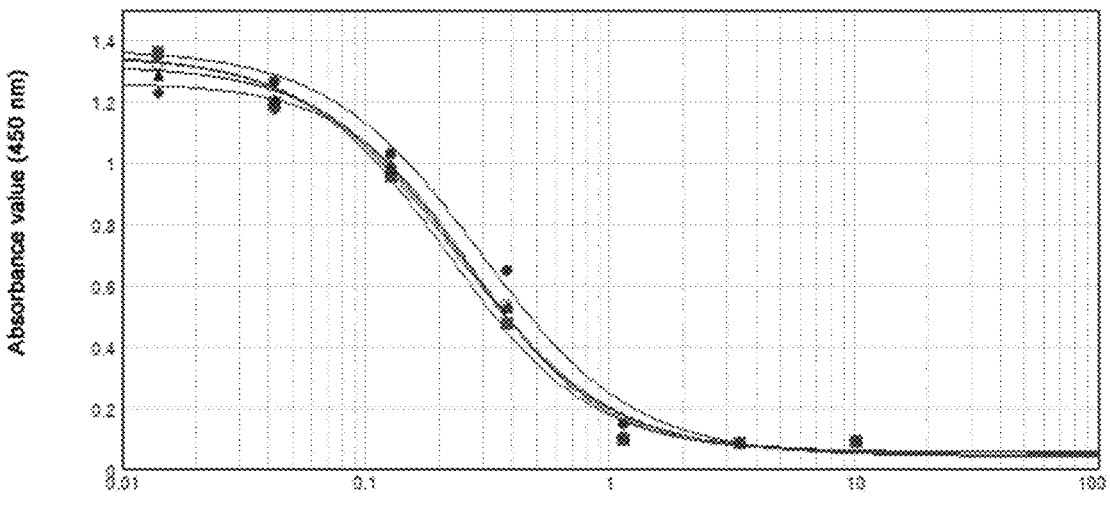
FIG. 4: the results of assays for the activity of antibodies 26B12H3L3, 26B12H1L4, 26B12H4L1 and 26B12H4L4 competing with human CD155-hFc-Biotin for binding to TIGIT-mFc.
Figure 5:
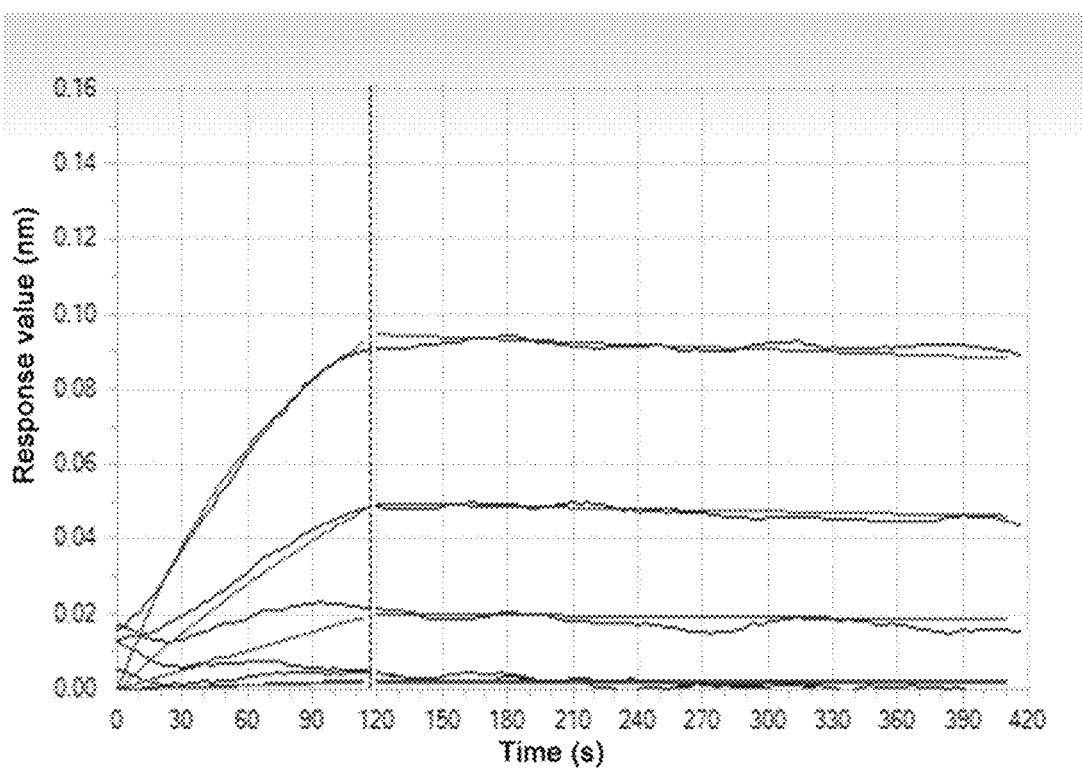
FIG. 5: the results of assays for the affinity constant of 26B12H3L3 for TIGIT-mFc. The antibody concentrations for the curve pairs from top to bottom are 5 nM, 1.67 nM, 0.557 nM, 0.185 nM and 0.06 nM, respectively.
Figure 6:
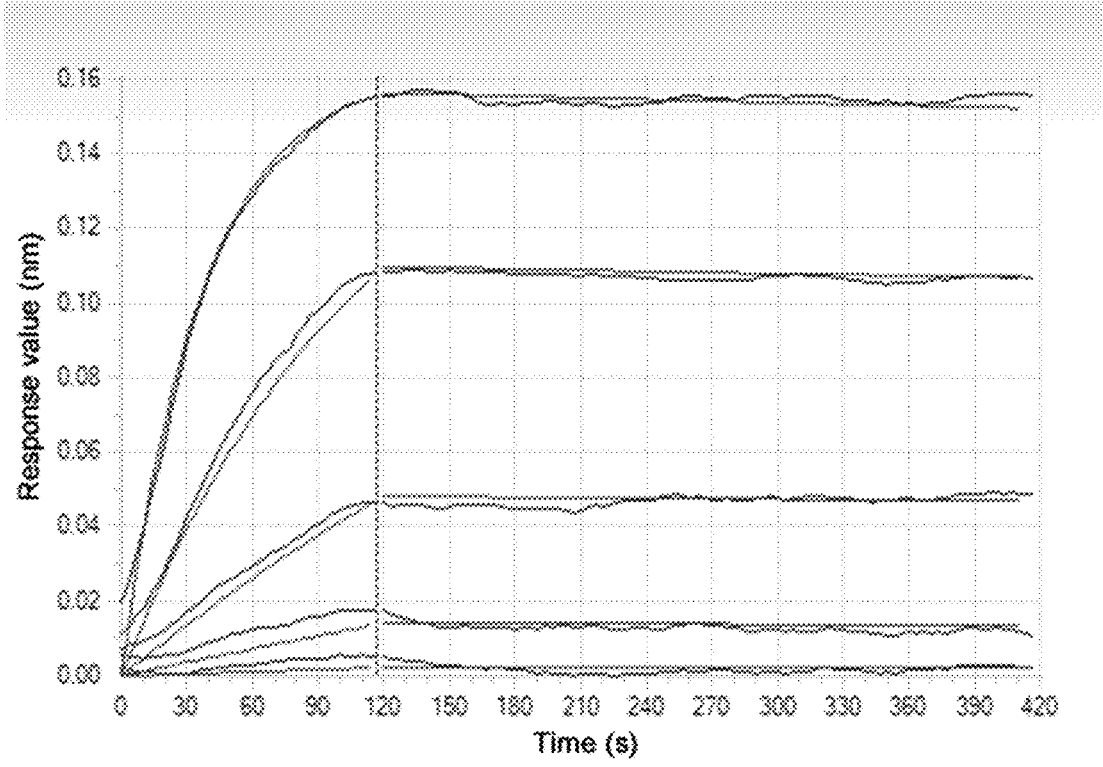
FIG. 6: the results of assays for the affinity constant of 26B12H1L1 for TIGIT-mFc. The antibody concentrations for the curve pairs from top to bottom are 5 nM, 1.67 nM, 0.557 nM, 0.185 nM and 0.06 nM, respectively.
Figure 7:
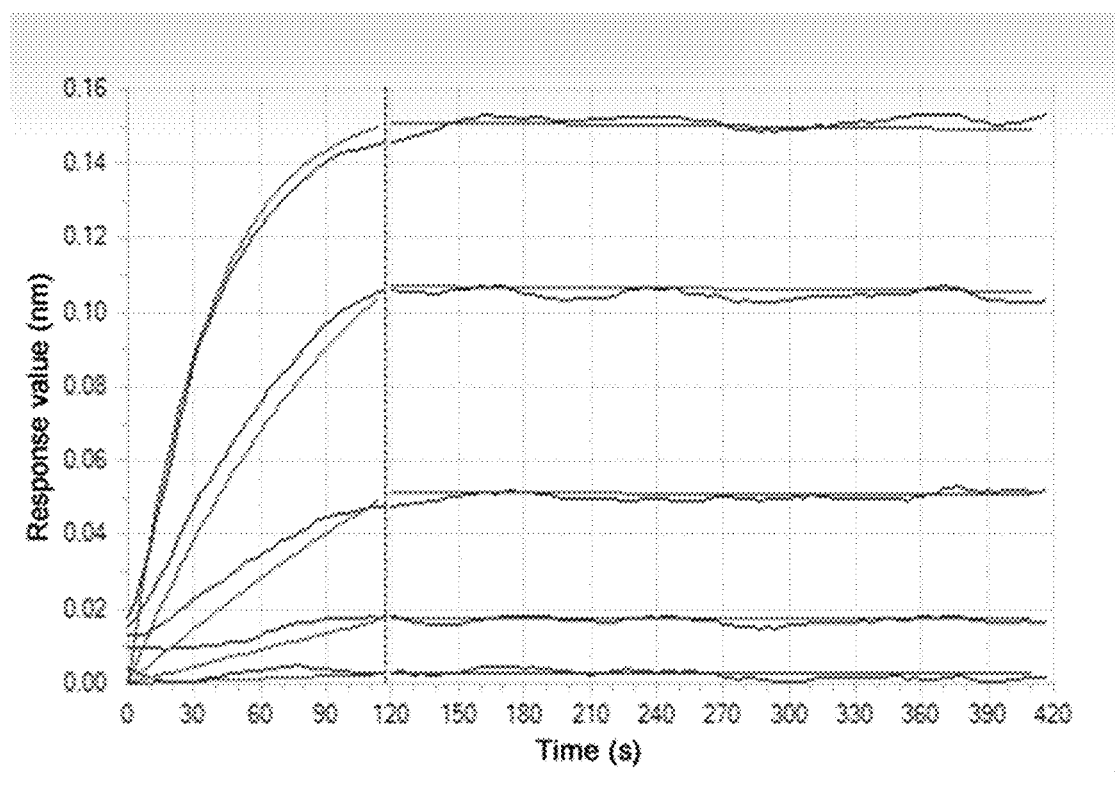
FIG. 7: the results of assays for the affinity constant of 26B12H2L2 for TIGIT-mFc. The antibody concentrations for the curve pairs from top to bottom are 5 nM, 1.67 nM, 0.557 nM, 0.185 nM and 0.06 nM, respectively.
Figure 8:
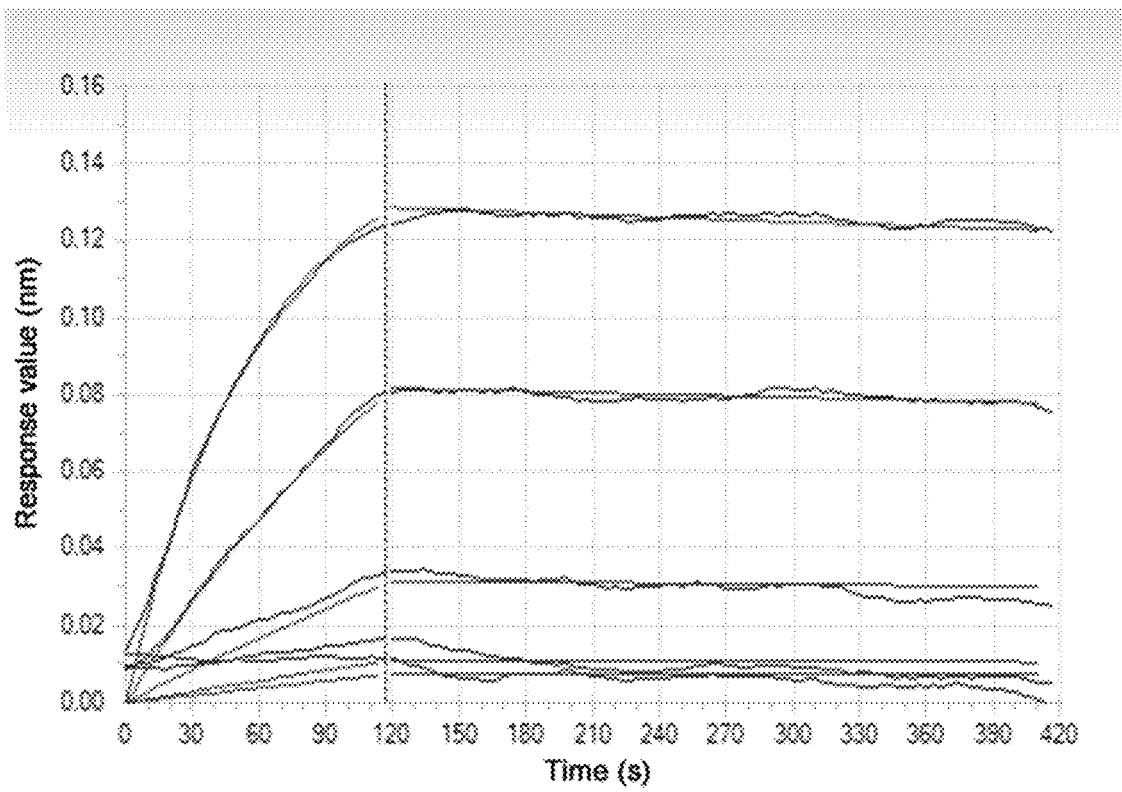
FIG. 8: the results of assays for the affinity constant of 26B12H2L3 for TIGIT-mFc. The antibody concentrations for the curve pairs from top to bottom are 5 nM, 1.67 nM, 0.557 nM, 0.185 nM and 0.06 nM, respectively.
Figures 9, 10:
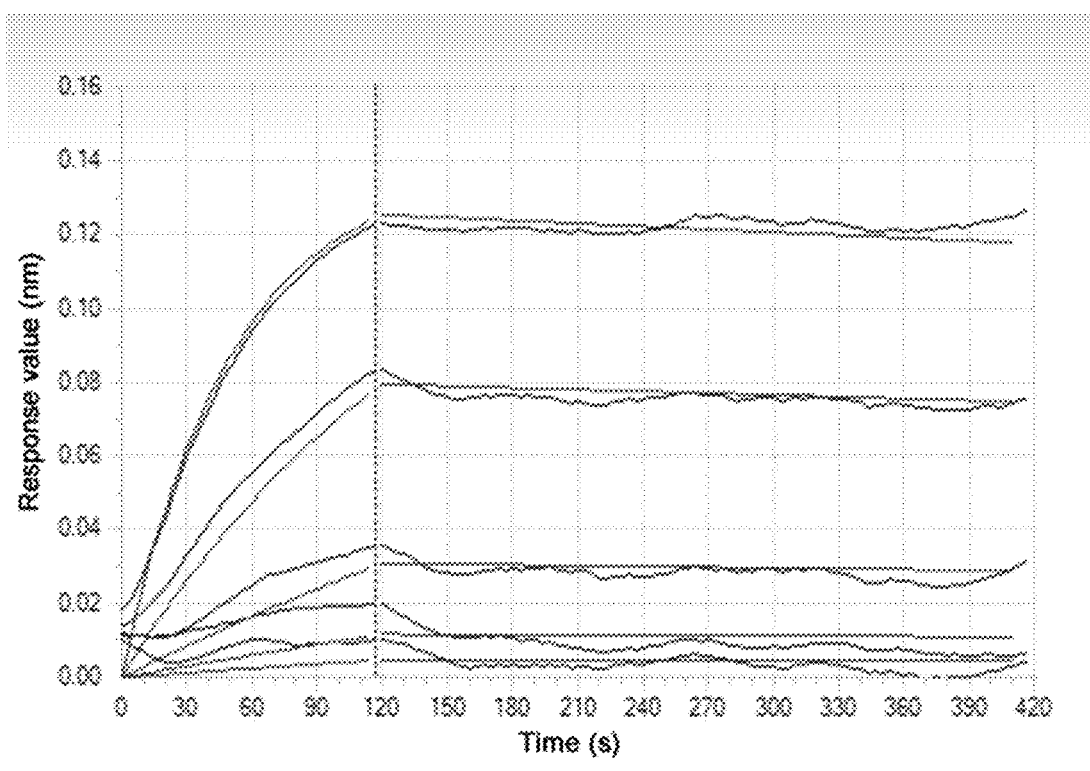
FIG. 9: the results of assays for the affinity constant of 26B12H3L2 for TIGIT-mFc. The antibody concentrations for the curve pairs from top to bottom are 5 nM, 1.67 nM, 0.557 nM, 0.185 nM and 0.06 nM, respectively.
FIG. 10: the results of assays for the affinity constant of 26B12H4L4 for TIGIT-mFc. The antibody concentrations for the curve pairs from top to bottom are 5 nM, 1.67 nM, 0.557 nM, 0.185 nM and 0.06 nM, respectively.
Figure 11:
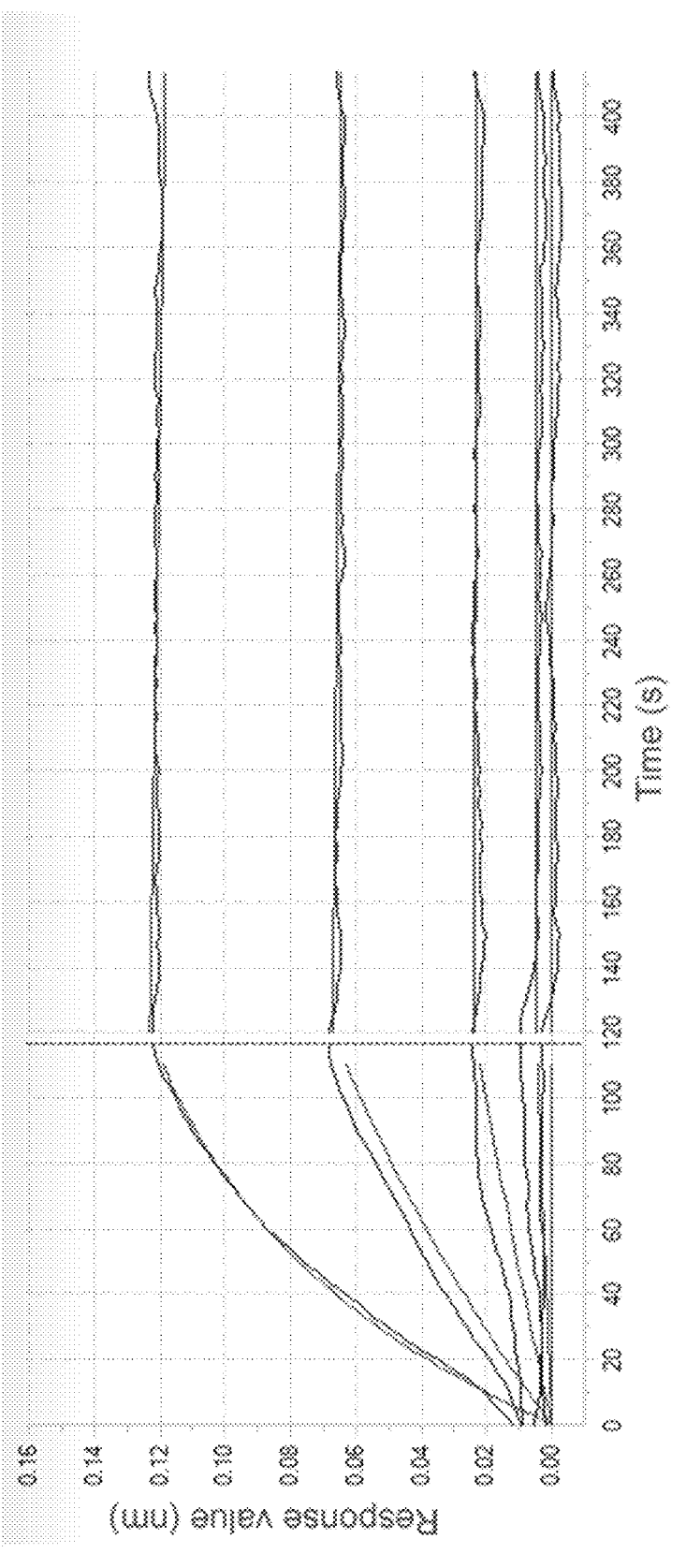
FIG. 11: the results of assays for the affinity constant of 26B12H1L4 for TIGIT-mFc. The antibody concentrations for the curve pairs from top to bottom are 5 nM, 1.67 nM, 0.557 nM, 0.185 nM and 0.06 nM, respectively.
Figure 12:
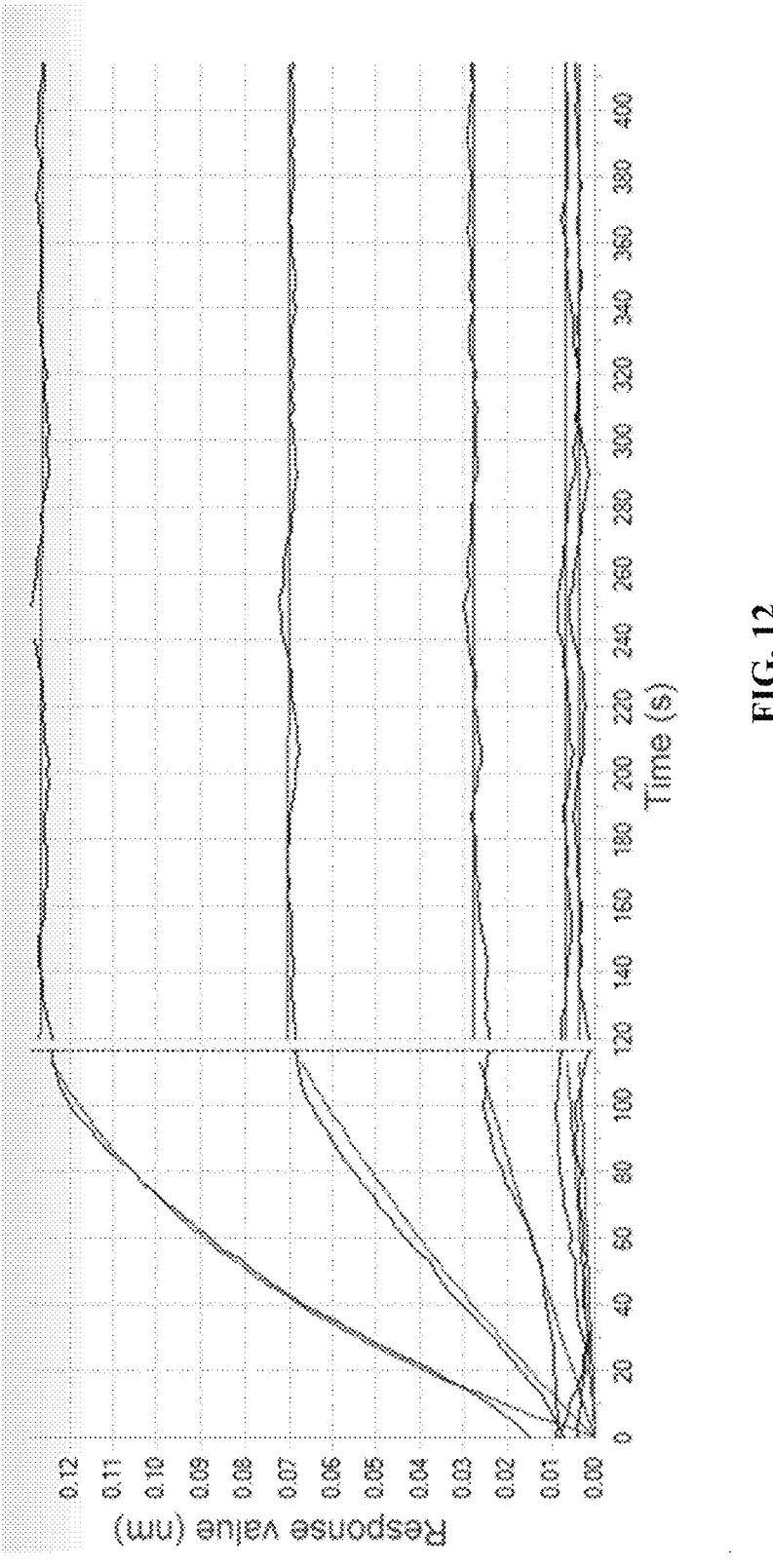
FIG. 12: the results of assays for the affinity constant of 26B12H4L1 for TIGIT-mFc. The antibody concentrations for the curve pairs from top to bottom are 5 nM, 1.67 nM, 0.557 nM, 0.185 nM and 0.06 nM, respectively.
Figure 13:
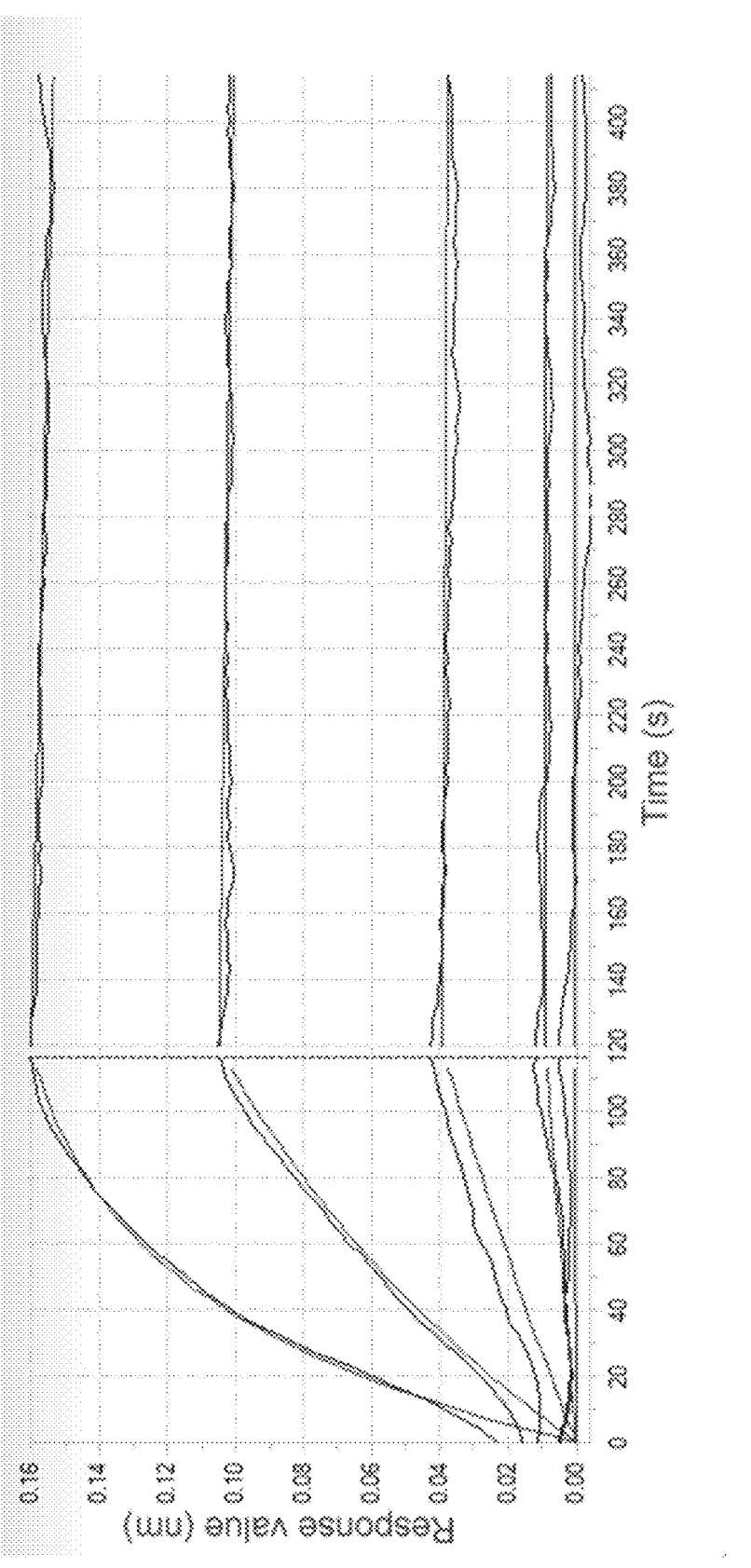
FIG. 13: the results of assays for the affinity constant of RG6058 for TIGIT-mFc. The antibody concentrations for the curve pairs from top to bottom are 5 nM, 1.67 nM, 0.557 nM, 0.185 nM and 0.06 nM, respectively.

The results of the activity of the antibodies competing with CD155-hFc-Biotin for binding to TIGIT-mFc are shown in Table 3 and Table 4. The $EC_{50}$ of the antibodies competing with CD155-hFc-Biotin for binding to TIGIT-mFc was calculated by curve fitting using antibody concentration as the abscissa and absorbance value as the ordinate, and the results are shown in Table 3 and Table 4, and FIG. 3 and FIG. 4 below.

TABLE 3

The results of assays for the activity of 26B12H1L1,
26B12H2L2, 26B12H2L3, 26B12H3L2 and RG6058 competing with
human CD155-hFc-Biotin for binding to TIGIT-mFc

| Antibody dilution | Antigen coating: TIGIT-mFc (2 µg/mL) | | | | | | | | | |
|---|---|---|---|---|---|---|---|---|---|---|
| | 26B12H1L1 | | 26B12H2L2 | | 26B12H2L3 | | 26B12H3L2 | | RG6058 | |
| 3 µg/mL | 0.091 | 0.097 | 0.101 | 0.110 | 0.106 | 0.117 | 0.107 | 0.113 | 0.119 | 0.120 |
| 1:3 | 0.088 | 0.085 | 0.082 | 0.092 | 0.098 | 0.100 | 0.101 | 0.102 | 0.104 | 0.112 |
| 1:9 | 0.104 | 0.099 | 0.091 | 0.097 | 0.107 | 0.110 | 0.121 | 0.120 | 0.114 | 0.121 |
| 1:27 | 0.533 | 0.491 | 0.410 | 0.538 | 0.510 | 0.537 | 0.492 | 0.549 | 0.528 | 0.532 |
| 1:81 | 1.026 | 1.035 | 0.996 | 1.025 | 0.961 | 0.990 | 0.948 | 1.059 | 0.951 | 1.011 |
| 1:243 | 1.210 | 1.251 | 1.222 | 1.221 | 1.142 | 1.195 | 1.089 | 1.217 | 1,168 | 1.209 |
| 1:729 | 1.287 | 1.360 | 1.274 | 1.242 | 1.201 | 1.287 | 1.120 | 1.236 | 1.209 | 1.251 |
| 0 | 1.347 | 1.387 | 1.315 | 1.296 | 1.279 | 1.307 | 1.263 | 1.340 | 1.295 | 1.354 |
| | CD155-hFc-Biotin (1 µg/mL) | | | | | | | | | |
| | SA-HRP (1:4000) | | | | | | | | | |
| $EC_{50}$ (nM) | 0.255 | | 0.254 | | 0.266 | | 0.283 | | 0.254 | |

TABLE 4

The results of assays for the activity of 26B12H3L3, 26B12H1L4, 26B12H4L1, 26B12H4L4 and RG6058 competing with human CD155-hFc-Biotin for binding to TIGIT-mFc

| Antibody dilution | Antigen coating: TIGIT-mFc (2 µg/mL) | | | | | | | | | |
| | 26B12H3L3 | | 26B12H1L4 | | 26B12H4L1 | | 26B12H4L4 | | RG6058 | |
| --- | --- | --- | --- | --- | --- | --- | --- | --- | --- | --- |
| 3 µg/mL | 0.087 | 0.085 | 0.091 | 0.084 | 0.102 | 0.086 | 0.091 | 0.085 | 0.091 | 0.093 |
| 1:3 | 0.083 | 0.082 | 0.077 | 0.086 | 0.086 | 0.086 | 0.084 | 0.082 | 0.089 | 0.084 |
| 1:9 | 0.139 | 0.146 | 0.094 | 0.096 | 0.106 | 0.102 | 0.103 | 0.103 | 0.101 | 0.100 |
| 1:27 | 0.646 | 0.650 | 0.449 | 0.495 | 0.495 | 0.561 | 0.516 | 0.532 | 0.530 | 0.539 |
| 1:81 | 1.031 | 1.027 | 0.938 | 0.967 | 0.931 | 1.030 | 0.974 | 0.999 | 0.946 | 1.037 |
| 1:243 | 1.239 | 1.294 | 1.171 | 1.224 | 1.180 | 1.232 | 1.131 | 1.218 | 1.152 | 1.223 |
| 1:729 | 1.318 | 1.378 | 1.336 | 1.382 | 1.278 | 1.292 | 1.123 | 1.335 | 1.302 | 1.346 |
| 0 | 1.410 | 1.393 | 1.341 | 1.361 | 1.357 | 1.360 | 1.258 | 1.364 | 1.380 | 1.427 |
| | CD155-hFc-Biotin (1 µg/mL) SA-HRP (1:4000) | | | | | | | | | |
| $EC_{50}$ (nM) | 0.294 | | 0.217 | | 0.250 | | 0.271 | | 0.236 | |

The results show that in the same experimental conditions, 26B12H1L1, 26B12H4L1, 26B12H2L2, 26B12H3L2, 26B12H2L3, 26B12H3L3, 26B12H1L4 and 26B12H4L4 can each compete with CD155-hFc-Biotin for binding to the antigen TIGIT-mFc, and the activities are comparable to that of the positive drug RG6058 for the same target, indicating shaking rate was 1000 rpm. The data were analyzed by 1:1 model fitting to obtain affinity constants.

The results of assays for the affinity constants of the humanized antibodies (as control antibody) for TIGIT are shown in Table 5 and FIGS. 5-13.

TABLE 5

The results of assays for the affinity constants of humanized antibodies for antigen TIGIT-mFc

| Antibody | Maximum signal height of analyte (nm) | $K_D$ (M) | kon (1/Ms) | S E (kon) | kdis (1/s) | S E (kdis) | Rmax (nm) |
| --- | --- | --- | --- | --- | --- | --- | --- |
| 26B12H3L3 | 0.09 | 9.64E−11 | 2.48E+06 | 3.22E+05 | 2.39E−04 | 8.57E−05 | 0.05-0.13 |
| 26B12H1L1 | 0.15 | 1.64E−11 | 5.44E+06 | 1.92E+05 | 8.93E−05 | 3.36E−05 | 0.06-0.17 |
| 26B12H2L2 | 0.14 | 8.40E−12 | 5.47E+06 | 2.55E+05 | 4.60E−05 | 4.40E−05 | 0.07-0.17 |
| 26B12H2L3 | 0.12 | 4.85E−11 | 3.29E+06 | 2.53E+05 | 1.59E−04 | 5.92E−05 | 0.15-0.31 |
| 26B12H3L2 | 0.12 | 5.40E−11 | 3.94E+06 | 3.60E+05 | 2.13E−04 | 7.86E−05 | 0.13-0.17 |
| 26B12H4L4 | 0.13 | 3.69E−11 | 2.81E+06 | 1.38E+05 | 1.04E−04 | 3.23E−05 | 0.14-0.20 |
| 26B12H1L4 | 0.12 | 4.63E−11 | 2.94E+06 | 1.96E+05 | 1.36E−04 | 4.88E−05 | 0.01-0.15 |
| 26B12H4L1 | 0.12 | 8.57E−12 | 2.90E+06 | 1.34E+05 | 2.48E−05 | 3.11E−05 | 0.11-0.18 |
| RG6058 | 0.16 | 3.16E−11 | 4.56E+06 | 1.84E+05 | 1.44E−04 | 3.46E−05 | 0.01-0.18 | that 26B12H1L1, 26B12H4L1, 26B12H2L2, 26B12H3L2, 26B12H2L3, 26B12H3L3, 26B12H1L4 and 26B12H4L4 have an effective function of competing with CD155-hFc-Biotin for binding to TIGIT-mFc.

Example 6: Assays for Kinetic Parameters of Humanized Antibodies 26B12H3L3, 26B12H1L1, 26B12H2L2, 26B12H2L3, 26B12H3L2, 26B12H4L4, 26B12H1L4, 26B12H4L1 and RG6058 Binding to Antigen TIGIT-mFc Using Fortebio Molecular Interaction Instrument The sample dilution buffer was PBS (0.02% Tween-20, 0.1% BSA, pH 7.4). TIGIT-mFc was immobilized on an AMC sensor at a concentration of 3 µg/mL for 50 s, and the sensor was equilibrated in the buffer for 60 s. The TIGIT-mFc immobilized on the sensor was allowed to bind to antibody at concentrations of 0.06-5 nM (three-fold dilutions) for 120 s, and the protein was dissociated in the buffer for 300 s. The sensor was regenerated with 10 mM glycine solution (pH=1.7). The detection temperature was 37° C., the detection frequency was 0.3 Hz, and the sample plate $K_D$ is the affinity constant; $K_D$=kdis/kon.

The results show that the affinity constants of humanized antibodies 26B12H3L3, 26B12H1L1, 26B12H2L2, 26B12H2L3, 26B12H3L2, 26B12H4L4, 26B12H1L4, 26B12H4L1 and RG6058 for TIGIT-mFc were 9.64E-11 M, 1.64E-11 M, 8.40E-12 M, 4.85E-11 M, 5.40E-11 M, 3.69E-11 M, 4.63E-11 M, 8.57E-12 M and 3.16E-11 M, respectively.

The results demonstrate that according to the level of affinity for TIGIT-mFc, the antibodies against TIGIT can be listed in a descending order as follows: 26B12H2L2, 26B12H4L1, 26B12H1L1, RG6058, 26B12H4L4, 26B12H1L4, 26B12H2L3, 26B12H3L2, 26B12H3L3. Among them, the humanized antibodies 26B12H2L2, 26B12H4L1 and 26B12H1L1 have stronger affinity than the positive drug RG6058, and 26B12H4L4 has comparable affinity to the positive drug RG6058.

Example 7: FACS Assays for Activity of
Humanized Antibodies 26B12H2L2 and RG6058
Binding to 293T-TIGIT Cell Membrane Surface
Antigen TIGIT Experimental Method:

The vector plenti6.3/V5-TIGITFL-BSD of TIGIT (the vector pLenti6.3 was purchased from Invitrogen) was transfected into 293T cells, and 293T-TIGIT cell line cells stably expressing TIGIT were obtained by screening.

293T-TIGIT cells were collected (DMEM+10% FBS) and centrifuged for 5 min, and the supernatant was discarded. The cells were resuspended and counted, and the cell viability was determined (P7, 95.79%). The cells were diluted, 300 thousand cells were added to each well of a transparent V-bottomed 96-well plate, and 200 μL of 1% PBSA was added to each tube. The mixtures were centrifuged for 5 min, and the supernatants were discarded. According to the experimental design, 100 μL of antibodies were added to each well (final concentration: 300 nM, 100 nM, 33.3 nM, 11.1 nM, 3.7 nM, 1.23 nM, 0.41 nM, 0.041 nM, and 0.0041 nM), and blank control and isotype control were designed. The plate was incubated on ice for 60 min. 200 μL of 1% PBSA was added to each tube. The mixtures were centrifuged for 5 min, and the supernatants were discarded. The plate was washed twice. FITC goat anti-human IgG antibody (diluted 500-fold with PBSA) was added to each sample, and the mixtures were incubated on ice in the dark for 40 min. 200 μL of PBSA was added to each tube. The mixtures were centrifuged for 5 min, and the supernatants were discarded. The cells were resuspended by adding 200 μL of PBSA, and the suspensions were transferred into flow cytometry tubes to measure the mean fluorescence intensity of the cells at each concentration by a flow cytometer.

The experimental results demonstrate that the humanized antibody 26B12H2L2 has a stronger binding ability to the cell membrane surface antigen TIGIT than the positive control antibody RG6058.

Example 8: FACS Assays for Activity of
Humanized Antibodies 26B12H2L2 and RG6058
Competing with CD155 or CD112 for Binding to
293T-TIGIT Cell Membrane Surface Antigen
TIGIT Experimental method: 293T-TIGIT cells were collected and centrifuged for 5 min, and the supernatant was discarded. The cells were resuspended and counted, and the cell viability was determined (94.95%). The cells were diluted, 300 thousand cells were added to each well of a transparent V-bottomed 96-well plate, and 200 μL of 1% PBSA was added to each tube. The mixtures were centrifuged for 5 min, and the supernatants were discarded. According to the experimental design, 100 μL of antibodies were added to each well (final concentration: 300 nM, 100 nM, 33.3 nM, 11.1 nM, 3.7 nM, 1.23 nM, 0.123 nM, and 0.0123 nM), and blank control and isotype control were designed. The plate was incubated on ice for 30 min. CD155 (final concentration: 10 nM) or CD112 (final concentration: 30 nM) was added to each sample, and the mixtures were incubated on ice in the dark for 60 min. 200 μL of 1% PBSA was then added to each tube. The mixtures were centrifuged for 5 min, and the supernatants were discarded. The plate was washed twice. APC goat anti-mouse IgG (minimal x-reactivity) antibody (diluted 300-fold with PBSA) was added to each sample, and the mixtures were incubated on ice in the dark for 40 min. 200 μL of PBSA was added to each tube. The

TABLE 6

FACS assays for the activity of humanized antibodies
26B12H2L2 and RG6058 binding to 293T-TIGIT cell membrane surface
antigen TIGIT-

| Antibody/ concentration | Mean fluorescence intensity | | | | | | | | | $EC_{50}$ |
|---|---|---|---|---|---|---|---|---|---|---|
| (nM) | 300 | 100 | 33.33 | 11.1 | 3.7 | 1.23 | 0.41 | 0.041 | 0.0041 | (nM) |
| RG6058 | 505.61 | 554.87 | 493.98 | 537.75 | 431.36 | 266.73 | 109.14 | 24.47 | 14.61 | 1.257 |
| 26B12H2L2 | 514.58 | 467.29 | 412.32 | 645.99 | 466.99 | 320.40 | 122.58 | 28.76 | 12.66 | 0.917 |

Figure 14:
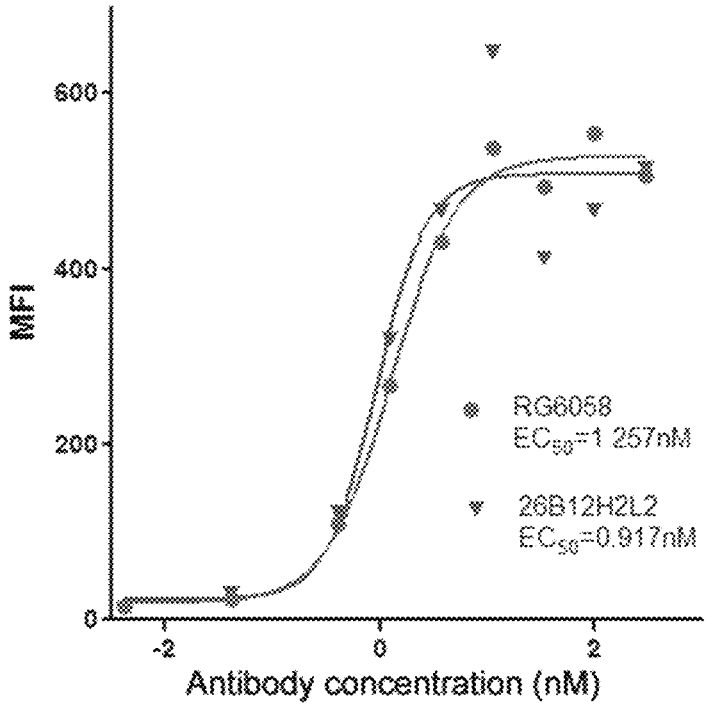
FIG. 14: FACS assays for the activity of humanized antibodies 26B12H2L2 and RG6058 binding to 293T-TIGIT cell membrane surface antigen TIGIT.

The experimental results are shown in Table 6 and FIG. 14. The $EC_{50}$ for binding of the positive control antibody RG6058 to the cell membrane surface antigen TIGIT was 1.257 nM, and the $EC_{50}$ for binding of the humanized antibody 26B12H2L2 to cell membrane surface antigen TIGIT—was 0.917 nM.

mixtures were centrifuged for 5 min, and the supernatants were discarded. The cells were resuspended by adding 200 μL of PBSA, and the suspensions were transferred into flow cytometry tubes to measure the mean fluorescence intensity of the cells at each concentration by a flow cytometer.

Figure 15:
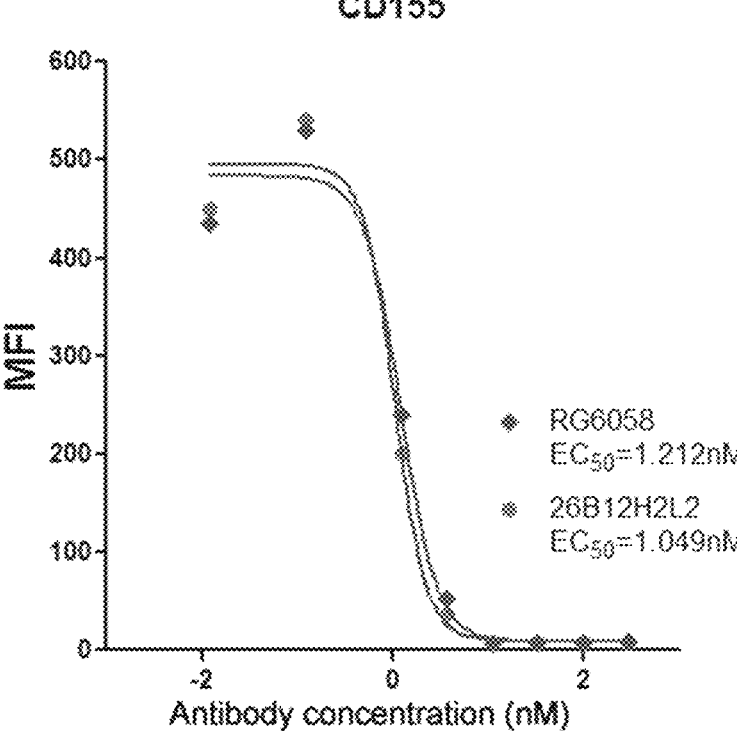
FIG. 15: FACS assays for the activity of humanized antibodies 26B12H2L2 and RG6058 competing with CD155 for binding to 293T-TIGIT cell membrane surface TIGIT.
Figure 16:
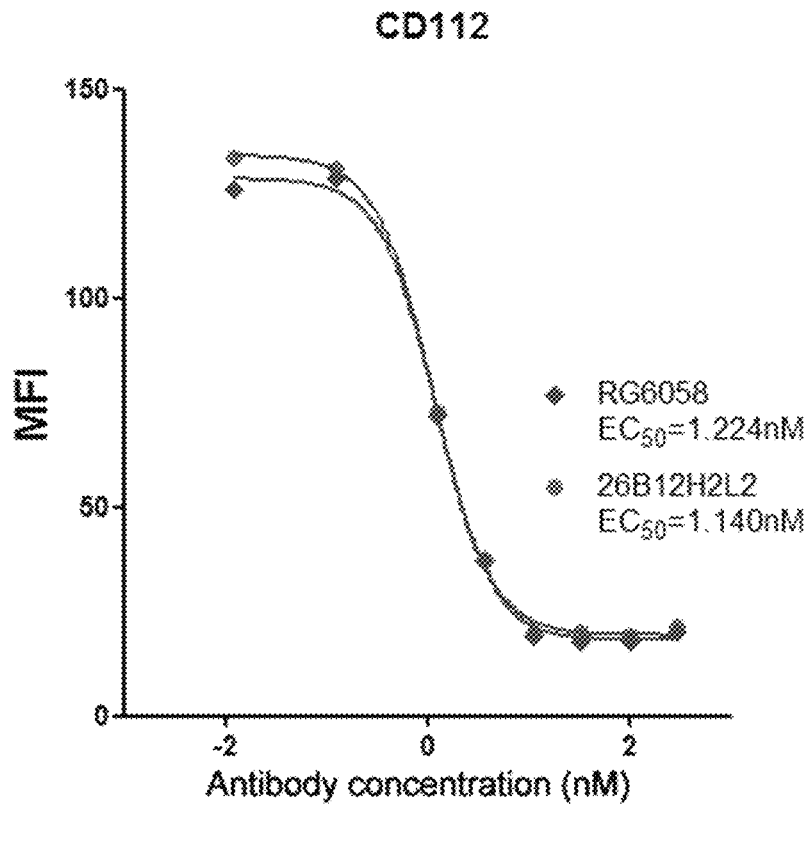
FIG. 16: FACS assays for the activity of humanized antibodies 26B12H2L2 and RG6058 competing with CD112 for binding to 293T-TIGIT cell membrane surface TIGIT.

The experimental results are shown in Table 7 and FIG. 15, as well as Table 8 and FIG. 16.

TABLE 7

FACS assays for the activity of humanized antibodies
26B12H2L2 and RG6058 competing with CD155 for binding to 293T-TIGIT cell
membrane surface antigen TIGIT

| Antibody/ concentration | Mean fluorescence intensity | | | | | | | | $EC_{50}$ |
|---|---|---|---|---|---|---|---|---|---|
| (nM) | 300 | 100 | 33.3 | 11.1 | 3.7 | 1.23 | 0.123 | 0.0123 | (nM) |
| RG6058 | 8.85 | 7.44 | 7.6 | 7.71 | 52.1 | 239 | 530 | 436 | 1.212 |
| 26B12H2L2 | 8.3 | 7.64 | 7.83 | 8.2 | 36.1 | 200 | 541 | 449 | 1.049 |

TABLE 8

| FACS assays for the activity of humanized antibodies 26B12H2L2 and RG6058 competing with CD112 for binding to 293T-TIGIT cell membrane surface antigen TIGIT | | | | | | | | | |
|---|---|---|---|---|---|---|---|---|---|
| Antibody/ concentration | Mean fluorescence intensity | | | | | | | | $EC_{50}$ |
| (nM) | 300 | 100 | 33.3 | 11.1 | 3.7 | 1.23 | 0.123 | 0.0123 | (nM) |
| RG6058 | 20.1 | 17.8 | 18 | 19.2 | 37.1 | 72 | 129 | 126 | 1.224 |
| 26B12H2L2 | 21.4 | 19.2 | 20.3 | 19.8 | 37.1 | 73.1 | 131 | 134 | 1.140 |

The results show that the $EC_{50}$ of the positive control antibody RG6058 competing with CD155 for binding to TIGIT was 1.212 nM, and the $EC_{50}$ of the humanized antibody 26B12H2L2 competing with CD155 for binding to TIGIT was 1.049 nM; the $EC_{50}$ of the positive control antibody RG6058 competing with CD112 for binding to TIGIT was 1.224 nM, and the $EC_{50}$ of the humanized antibody 26B12H2L2 competing with CD112 for binding to TIGIT was 1.140 nM.

The experimental results demonstrate that the humanized antibody 26B12H2L2 has stronger ability to compete with CD155 or CD112 for binding to the cell membrane surface antigen TIGIT than the positive control antibody RG6058.

Example 9: Mixed Lymphocyte Reaction after Adding TIGIT Antibodies to Jurkat-TIGIT and HT1080-aCD3scFv Cell Systems Experimental Method:

The vector plenti6.3/V5-TIGITFL-BSD of TIGIT (the vector pLenti6.3 was purchased from Invitrogen) was transfected into Jurkat cells, and Jurkat-TIGIT cell line cells stably expressing TIGIT were obtained by screening; the vector pCDH-aCD3scFv-puro of the anti-CD3 antibody (the vector pCDH-CMV-MCS-EF1-Puro was purchased from Youbio) was transfected into HT-1080 cells, and HT1080-aCD3scFv cell line cells stably expressing anti-CD3scFv was obtained by screening.

Jurkat-TIGIT and HT1080-aCD3scFv cells in logarithmic growth phase were collected. In 96-well plates, 50 thousand Jurkat-TIGIT cells were added to each well, and 10 thousand HT1080-aCD3scFV cells were added to each well. The diluted antibodies (final concentration: 10 nM, 50 nM, and 250 nM) and anti-human CD28 antibody (3 μg/mL) were added. The plates were incubated in an incubator for 48 h. The culture supernatants were collected and assayed for IL-2 content using IL-2 ELISA kit.

Figure 17:
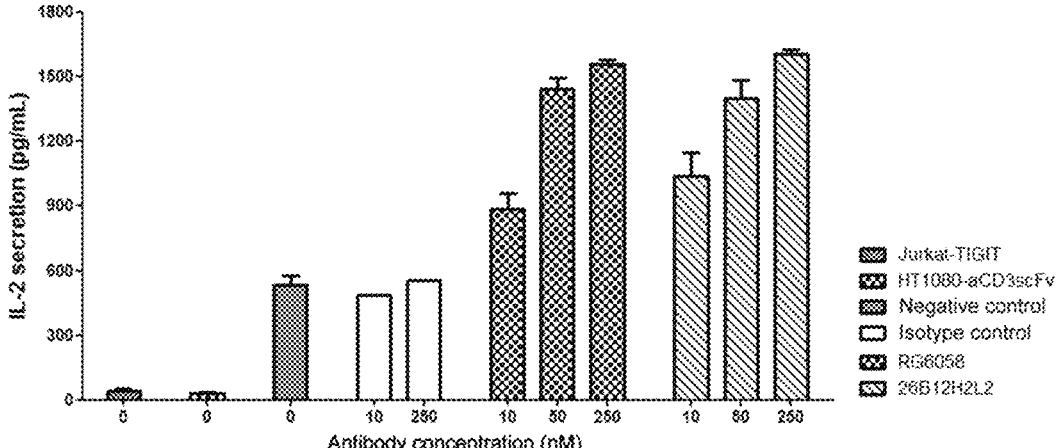
FIG. 17: the levels of IL-2 secretion after addition of TIGIT antibodies to Jurkat-TIGIT and HT1080-aCD3scFv systems.

The experimental results are shown in FIG. 17.

The results show that the humanized antibody 26B12H2L2 and the positive control antibody RG6058 could both promote IL-2 secretion in the systems, and the humanized antibody 26B12H2L2 promoted IL-2 secretion to similar levels to RG6058 at these concentrations (10 nM, 50 nM, and 250 nM).

The results demonstrate that the ability of the humanized antibody 26B12H2L2 to induce the IL-2 secretion of the cells is comparable to that of the positive control antibody RG6058.

Example 10: Therapeutic Effect of 26B12H2L2 on CT26 Mouse Xenograft Tumors in hTigit-BALB/c Transgenic Mice hTigit-BALB/c transgenic mice (purchased from Gempharmatech Co., Ltd, in which the normal mouse TIGIT gene was replaced by the human TIGIT gene) were each inoculated with 500 thousand CT26 cells (mouse colon cancer cell line, purchased from ATCC) in the back. Specifically, a mouse tumor model was established by inoculating 100 μL of 50 million/mL CT26 cells into each mouse. The experimental mice were divided into the following groups of 8 mice:

isotype control group G1, administered at a dose of 20 mg/kg by intraperitoneal injection (i.p.) twice weekly;

experimental group G2, administered at a dose of 4 mg/kg by intraperitoneal injection (i.p.) twice weekly;

experimental group G3, administered at a dose of 20 mg/kg by intraperitoneal injection (i.p.) twice weekly; and positive control group G4, administered at a dose of 20 mg/kg by intraperitoneal injection (i.p.) twice weekly.

The specific regimen is shown in Table 9.

TABLE 9

| Establishment of mouse CT26 tumor model and administration regimen of antibodies | | | | |
|---|---|---|---|---|
| Group | Number of cells | Number of animals | Modeling | Administration regimen |
| G1 | 500 thousand cells/mouse | 8 | CT26 cells: 50 million cells/mL | hIgG1 20 mg/kg, Intraperitoneal injection (i.p.), twice weekly |
| G2 | 500 thousand cells/mouse | 8 | Inoculation volume: 100 μL/mouse | 26B12H2L2 4 mg/kg, intraperitoneal injection (i.p.), twice weekly |
| G3 | 500 thousand cells/mouse | 8 | Inoculation volume: 100 μL/mouse | 26B12H2L2 20 mg/kg, intraperitoneal injection (i.p.), twice weekly |
| G4 | 500 thousand cells/mouse | 8 | Inoculation volume: 100 μL/mouse | RG6058 20 mg/kg, intraperitoneal injection (i.p.), twice weekly |

Figure 18:
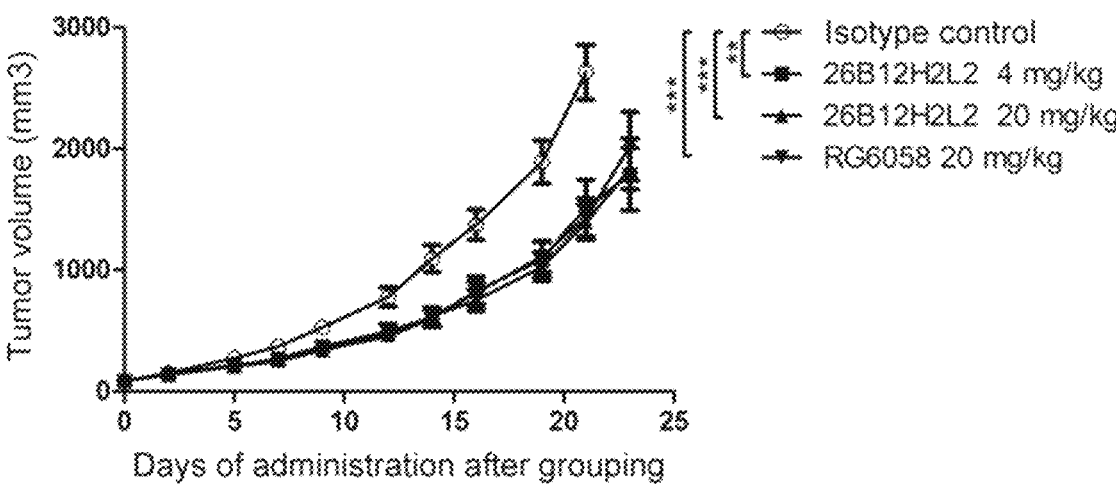
FIG. 18: the effect on hTIGIT-BALB/c transgenic mouse CT26 tumor model.

The experimental results are shown in FIG. 18.

The results show that 26B12H2L2 and RG6058 caused significant reductions in tumor volume in the hTIGIT-BALB/c transgenic mouse CT26 tumor model compared to the isotype control.

The results demonstrate that 26B12H2L2 has a very strong drug effect on the hTIGIT-BALB/c transgenic mouse CT26 tumor model, and the effect is comparable to that of RG6058, so 26B12H2L2 has the potential to treat and/or prevent tumors, particularly colon cancer.

Figure 19:
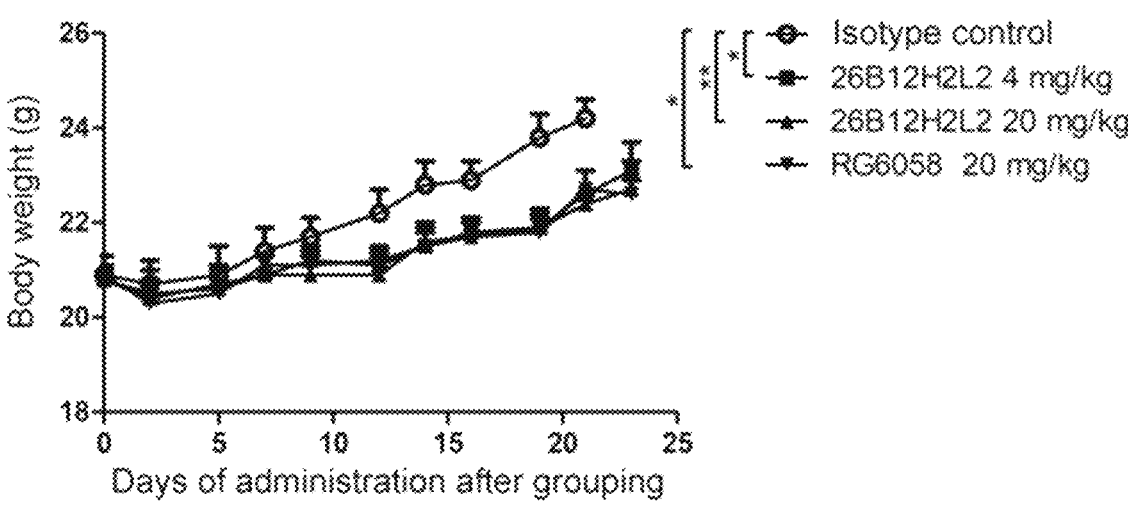
FIG. 19: the changes in body weight of hTIGIT-BALB/c transgenic mice CT26 tumor model.

Meanwhile, as shown in FIG. 19, 26B12H2L2 had no effect on the body weight of the hTIGIT-BALB/c transgenic mice as the CT26 tumor model, indicating that the antibody 26B12H2L2 did not cause toxic side effects on the mice.

Although specific embodiments of the present invention have been described in detail, those skilled in the art will appreciate that various modifications and substitutions can be made to those details according to all the teachings that have been disclosed, and these changes shall all fall within the protection scope of the present invention. The full scope of the present invention is given by the appended claims and any equivalent thereof.

The invention claimed is:

1. An anti-TIGIT antibody or an antigen-binding fragment thereof,
    wherein the anti-TIGIT antibody comprises a heavy chain variable region and a light chain variable region,
    wherein the heavy chain variable region of the antibody comprises HCDR1-HCDR3 with amino acid sequences set forth in SEQ ID NOs: 3-5, respectively, and the light chain variable region of the antibody comprises LCDR1-LCDR3 with amino acid sequences set forth in SEQ ID NOs: 8-10, respectively.

2. The anti-TIGIT antibody or the antigen-binding fragment thereof according to claim 1, wherein the heavy chain variable region of the antibody comprises an amino acid sequence selected from SEQ ID NO: 1, SEQ ID NO: 11, SEQ ID NO: 13, SEQ ID NO: 15, and SEQ ID NO: 17; and
    the light chain variable region of the antibody comprises an amino acid sequence selected from SEQ ID NO: 6, SEQ ID NO: 19, SEQ ID NO: 21, SEQ ID NO: 23, and SEQ ID NO: 25.

3. The anti-TIGIT antibody or the antigen-binding fragment thereof according to claim 1, wherein
    the heavy chain variable region of the antibody comprises an amino acid sequence set forth in SEQ ID NO: 1, and the light chain variable region of the antibody comprises an amino acid sequence set forth in SEQ ID NO: 6;
    the heavy chain variable region of the antibody comprises an amino acid sequence set forth in SEQ ID NO: 11, and the light chain variable region of the antibody comprises an amino acid sequence set forth in SEQ ID NO: 19;
    the heavy chain variable region of the antibody comprises an amino acid sequence set forth in SEQ ID NO: 17, and the light chain variable region of the antibody comprises an amino acid sequence set forth in SEQ ID NO: 19;
    the heavy chain variable region of the antibody comprises an amino acid sequence set forth in SEQ ID NO: 13, and the light chain variable region of the antibody comprises an amino acid sequence set forth in SEQ ID NO: 21;
    the heavy chain variable region of the antibody comprises an amino acid sequence set forth in SEQ ID NO: 13, and the light chain variable region of the antibody comprises an amino acid sequence set forth in SEQ ID NO: 23;
    the heavy chain variable region of the antibody comprises an amino acid sequence set forth in SEQ ID NO: 15, and the light chain variable region of the antibody comprises an amino acid sequence set forth in SEQ ID NO: 21;
    the heavy chain variable region of the antibody comprises an amino acid sequence set forth in SEQ ID NO: 15, and the light chain variable region of the antibody comprises an amino acid sequence set forth in SEQ ID NO: 23;
    the heavy chain variable region of the antibody comprises an amino acid sequence set forth in SEQ ID NO: 11, and the light chain variable region of the antibody comprises an amino acid sequence set forth in SEQ ID NO: 25; or
    the heavy chain variable region of the antibody comprises an amino acid sequence set forth in SEQ ID NO: 17, and the light chain variable region of the antibody comprises an amino acid sequence set forth in SEQ ID NO: 25.

4. The anti-TIGIT antibody or the antigen-binding fragment thereof according to claim 1, wherein the anti-TIGIT antibody or the antigen-binding fragment thereof is selected from Fab, Fab', F(ab')$_2$, Fv, a single chain antibody, a humanized antibody, a chimeric antibody, and a diabody.

5. The anti-TIGIT antibody or the antigen-binding fragment thereof according to claim 1, wherein
    the antibody comprises a one or more human framework region.

6. The anti-TIGIT antibody or the antigen-binding fragment thereof according to claim 1, wherein the anti-TIGIT antibody comprises a heavy chain constant region and a light chain constant region, wherein the heavy chain constant region of the antibody is Ig gamma-1 chain C region or Ig gamma-4 chain C region; and the light chain constant region of the antibody is Ig kappa chain C region.

7. The anti-TIGIT antibody or the antigen-binding fragment thereof according to claim 1, wherein the antibody binds to TIGIT-mFc with a K$_D$ of less than 4E-10 or less than 4E-11; wherein the K$_D$ is measured by a Fortebio molecular interaction instrument.

8. The anti-TIGIT antibody or the antigen-binding fragment thereof according to claim 1, wherein the antibody binds to TIGIT-mFc with an EC$_{50}$ of less than 1.5 nM, less than 1.2 nM, or less than 1 nM; wherein the EC$_{50}$ is measured by a flow cytometer.

9. The anti-TIGIT antibody or the antigen-binding fragment thereof according to claim 1, wherein the anti-TIGIT antibody is an antibody produced by a hybridoma cell line LT019 deposited at China Center for Type Culture Collection (CCTCC) under CCTCC NO. C2020208.

10. An isolated nucleic acid molecule, encoding the anti-TIGIT antibody or the antigen-binding fragment according to claim 1.

11. A vector, comprising the isolated nucleic acid molecule according to claim 10.

12. A host cell, comprising the isolated nucleic acid molecule according to claim 10.

13. A hybridoma cell line LT019 deposited at China Center for Type Culture Collection (CCTCC) under CCTCC NO. C2020208.

14. A conjugate, comprising an antibody and a conjugated moiety, wherein the antibody is the anti-TIGIT antibody or the antigen-binding fragment thereof according to claim 1, and the conjugated moiety is a detectable label.

15. A kit, comprising the anti-TIGIT antibody or the antigen-binding fragment thereof according to claim 1;

wherein the kit further comprises a secondary antibody specifically recognizing the anti-TIGIT antibody; wherein the secondary antibody further comprises a detectable label.

16. A bispecific antibody, comprising a first protein functional region and a second protein functional region, wherein the first protein functional region targets TIGIT;

the second protein functional region targets a target other than TIGIT;

wherein the first protein functional region is the antibody or the antigen-binding fragment according to claim 1.

17. The bispecific antibody according to claim 16, wherein the first protein functional region and the second protein functional region are linked directly or via a linker fragment.

18. The bispecific antibody according to claim 16, comprising 1, 2, or more first protein functional region and, independently, 1, 2 or more second protein functional region.

19. A pharmaceutical composition, comprising the anti-TIGIT antibody or the antigen-binding fragment thereof according to claim 1, and a pharmaceutically acceptable carrier and/or excipient.

20. The pharmaceutical composition according to claim 19, further comprising one or more anti-PD-1 antibodies, or one or more anti-PD-L1 antibodies.

21. The pharmaceutical composition according to claim 19, wherein a mass ratio of the anti-TIGIT antibody or the antigen-binding fragment thereof to the anti-PD-1 antibody or the anti-PD-L1 antibody is (1:5)-(5:1), based on the mass of the antibodies.

22. A combination product, comprising a first product and a second product in separate packages, wherein the first product comprises the anti-TIGIT antibody or the antigen-binding fragment thereof according to claim 1;

the second product comprises at least one anti-PD-1 antibody or at least one anti-PD-L1 antibody;

wherein the first product and the second product further independently comprise one or more pharmaceutically acceptable adjuvants.

23. The combination product according to claim 22, wherein a mass ratio of the anti-TIGIT antibody or the antigen-binding fragment thereof to the anti-PD-1 antibody or the anti-PD-L1 antibody is (1:5)-(5:1), based on the mass of the antibodies.

24. A method for treating a cancer, comprising a step of administering to a subject in need an effective amount of the antibody or the antigen-binding fragment thereof according to claim 1, wherein the cancer is selected from one or more of ovarian cancer, colorectal cancer and multiple myeloma.

25. A method for treating a cancer, comprising a step of administering to a subject in need an effective amount of the antibody or the antigen-binding fragment thereof according to claim 16, wherein the cancer is selected from one or more of ovarian cancer, colorectal cancer and multiple myeloma.

26. The bispecific antibody according to claim 16, wherein the second protein functional region targets PD-1.

27. The bispecific antibody according to claim 16, wherein the bispecific antibody is in an IgG-scFv format.

28. The bispecific antibody according to claim 16, wherein the first protein functional region is an immunoglobulin, and the second protein functional region is a single chain antibody; or the first protein functional region is a single chain antibody, and the second protein functional region is an immunoglobulin.

29. The bispecific antibody according to claim 28, wherein (a) the first protein functional region is an immunoglobulin comprising two heavy chains and the second protein functional region is a single chain antibody linked to C-termini of two heavy chains; or (b) the second protein functional region is an immunoglobulin comprising two heavy chains and the first protein functional region is a single chain antibody linked to C-termini of two heavy chains.

* * * * *

```
                        SEQUENCE LISTING

<160> NUMBER OF SEQ ID NOS: 26

<210> SEQ ID NO 1
<211> LENGTH: 121
<212> TYPE: PRT
<213> ORGANISM: Artificial Sequence
<220> FEATURE:
<223> OTHER INFORMATION: 26B12VH

<400> SEQUENCE: 1

Glu Val Gln Leu Gln Glu Ser Gly Pro Gly Leu Val Lys Pro Ser Gln
1               5                   10                  15

Ser Leu Ser Leu Thr Cys Thr Val Thr Gly His Ser Phe Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Ser Tyr Ser Asp Ser Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Met Asn Ser Val Thr Thr Glu Asp Thr Ala Thr Tyr Tyr Cys
                85                  90                  95

Ala Arg Leu Asp Tyr Gly Asn Tyr Gly Gly Ala Met Asp Tyr Trp Gly
            100                 105                 110

Gln Gly Thr Ser Val Thr Val Ser Ser
        115                 120

<210> SEQ ID NO 2
<211> LENGTH: 363
<212> TYPE: DNA
<213> ORGANISM: Artificial Sequence
<220> FEATURE:
<223> OTHER INFORMATION: 26B12VH

<400> SEQUENCE: 2
gaggtgcagc tgcaggagtc tggacctggc ctggtgaaac cctctcagtc tctgtccctc      60
acctgcactg tcactggcca ctcattcacc agtgattatg cctggaactg gatccggcag     120
tttccaggaa acagactgga gtggatgggc tacataagct acagtgatag cactaactac     180
aacccatctc tcaaaagtcg aatctctatc actcgagaca catccaagaa ccagttcttc     240
ttgcagatga attctgtgac tactgaggac acagccacat attactgtgc aagattggac     300
tatggtaact acggtggggc tatggactac tggggtcaag ggacctcagt caccgtctcc     360
tca                                                                    363

<210> SEQ ID NO 3
<211> LENGTH: 9
<212> TYPE: PRT
<213> ORGANISM: Artificial Sequence
<220> FEATURE:
<223> OTHER INFORMATION: HCDR1

<400> SEQUENCE: 3

Gly His Ser Phe Thr Ser Asp Tyr Ala
1               5
```

<210> SEQ ID NO 4
<211> LENGTH: 7
<212> TYPE: PRT
<213> ORGANISM: Artificial Sequence
<220> FEATURE:
<223> OTHER INFORMATION: HCDR2

<400> SEQUENCE: 4

Ile Ser Tyr Ser Asp Ser Thr
1               5

<210> SEQ ID NO 5
<211> LENGTH: 14
<212> TYPE: PRT
<213> ORGANISM: Artificial Sequence
<220> FEATURE:
<223> OTHER INFORMATION: HCDR3

<400> SEQUENCE: 5

Ala Arg Leu Asp Tyr Gly Asn Tyr Gly Gly Ala Met Asp Tyr
1               5                   10

<210> SEQ ID NO 6
<211> LENGTH: 107
<212> TYPE: PRT
<213> ORGANISM: Artificial Sequence
<220> FEATURE:
<223> OTHER INFORMATION: 26B12VL

<400> SEQUENCE: 6

Asp Ile Val Leu Thr Gln Ser His Glu Phe Met Ser Thr Ser Leu Arg
1               5                   10                  15

Asp Arg Val Ser Ile Thr Cys Lys Ser Ser Gln His Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Lys Ala
65                  70                  75                  80

Glu Asp Leu Ala Val Tyr Tyr Cys Gln Gln His Tyr Ile Thr Pro Trp
                85                  90                  95

Thr Phe Gly Gly Gly Thr Lys Leu Glu Ile Lys
            100                 105

<210> SEQ ID NO 7
<211> LENGTH: 321
<212> TYPE: DNA
<213> ORGANISM: Artificial Sequence
<220> FEATURE:
<223> OTHER INFORMATION: 26B12VL

<400> SEQUENCE: 7
gatattgtgc taactcagtc tcacgaattc atgtccacct cattacgaga cagggtcagc        60
atcacctgca aatccagtca acatgtgagt actgctgtag cctggtatca acagaaacca       120
ggacaatctc ctaaactact gatttactcg gcatcctacc ggtacactgg agtccctgat       180
cgcttcactg gcagtggatc tgggacggat ttcactttca ccatcagcag tgtgaaggct       240
gaagacctgg cagtttatta ctgtcagcaa cattatatta ctccgtggac gttcggtgga       300
ggcaccaagc tggaaataaa a                                                  321

```
<210> SEQ ID NO 8
<211> LENGTH: 6
<212> TYPE: PRT
<213> ORGANISM: Artificial Sequence
<220> FEATURE:
<223> OTHER INFORMATION: LCDR1

<400> SEQUENCE: 8

Gln His Val Ser Thr Ala
1               5

<210> SEQ ID NO 9
<211> LENGTH: 3
<212> TYPE: PRT
<213> ORGANISM: Artificial Sequence
<220> FEATURE:
<223> OTHER INFORMATION: LCDR2

<400> SEQUENCE: 9

Ser Ala Ser
1

<210> SEQ ID NO 10
<211> LENGTH: 9
<212> TYPE: PRT
<213> ORGANISM: Artificial Sequence
<220> FEATURE:
<223> OTHER INFORMATION: LCDR3

<400> SEQUENCE: 10

Gln Gln His Tyr Ile Thr Pro Trp Thr
1               5

<210> SEQ ID NO 11
<211> LENGTH: 121
<212> TYPE: PRT
<213> ORGANISM: Artificial Sequence
<220> FEATURE:
<223> OTHER INFORMATION: 26B12H1

<400> SEQUENCE: 11

Asp Val Gln Leu Gln Glu Ser Gly Pro Gly Leu Val Lys Pro Ser Gln
1               5                   10                  15

Thr Leu Ser Leu Thr Cys Thr Val Ser Gly His Ser Phe Thr Ser Asp
            20                  25                  30

Tyr Ala Trp Asn Trp Ile Arg Gln Phe Pro Gly Lys Gly Leu Glu Trp
        35                  40                  45

Ile Gly Tyr Ile Ser Tyr Ser Asp Ser Thr Asn Tyr Asn Pro Ser Leu
    50                  55                  60

Lys Ser Arg Ile Thr Ile Ser Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Leu Asp Tyr Gly Asn Tyr Gly Gly Ala Met Asp Tyr Trp Gly
            100                 105                 110

Gln Gly Thr Ser Val Thr Val Ser Ser
        115                 120

<210> SEQ ID NO 12
<211> LENGTH: 363
<212> TYPE: DNA
<213> ORGANISM: Artificial Sequence
<220> FEATURE:
```

<223> OTHER INFORMATION: 26B12H1

<400> SEQUENCE: 12

```
gatgtgcagc tgcaggagag cggccccgga ctggtgaagc cttcccagac cctgtctctg      60
acctgtacag tgtctggcca cagcttcaca tccgactacg cctggaactg gatcaggcag     120
tttccaggca agggcctgga gtggatcggc tacatctctt atagcgactc caccaactat     180
aatccctctc tgaagagccg gatcaccatc agcagagata catccaagaa ccagttcttt     240
ctgcagctga acagcgtgac agccgccgac accgccacat actattgcgc ccggctggac     300
tacggcaatt atggcggagc catggattac tggggccagg gcacctccgt gacagtgagc     360
tcc                                                                   363
```

```
<210> SEQ ID NO 13
<211> LENGTH: 121
<212> TYPE: PRT
<213> ORGANISM: Artificial Sequence
<220> FEATURE:
<223> OTHER INFORMATION: 26B12H2
```

<400> SEQUENCE: 13

```
Asp Val Gln Leu Gln Glu Ser Gly Pro Gly Leu Val Lys Pro Ser Gln
1               5                   10                  15

Thr Leu Ser Leu Thr Cys Thr Val Ser Gly His Ser Phe Thr Ser Asp
                20                  25                  30

Tyr Ala Trp Ser Trp Ile Arg Gln Pro Pro Gly Lys Gly Leu Glu Trp
            35                  40                  45

Ile Gly Tyr Ile Ser Tyr Ser Asp Ser Thr Asn Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Gly Asn Tyr Gly Gly Ala Met Asp Tyr Trp Gly
            100                 105                 110

Gln Gly Thr Ser Val Thr Val Ser Ser
        115                 120
```

```
<210> SEQ ID NO 14
<211> LENGTH: 363
<212> TYPE: DNA
<213> ORGANISM: Artificial Sequence
<220> FEATURE:
<223> OTHER INFORMATION: 26B12H2
```

<400> SEQUENCE: 14

```
gatgtgcagc tgcaggagtc tggcccagga ctggtgaagc caagccagac cctgtccctg      60
acctgtacag tgtccggcca ctcttttaca agcgactacg cctggtcttg gatcaggcag     120 cccccctggca agggactgga gtggatcggc tacatctcct attctgacag caccaactat     180
aatccctccc tgaagtctcg ggtgaccatc tctagagata caagcaagaa ccagttctcc     240
ctgaagctga gtccgtgac cgcagcagac acagccgtgt actattgcgc ccggctggac     300
tacggcaatt atggcggagc catggattac tggggccagg gcaccagcgt gacagtgtct     360
agc                                                                   363
```

```
<210> SEQ ID NO 15
<211> LENGTH: 121
```

```
<212> TYPE: PRT
<213> ORGANISM: Artificial Sequence
<220> FEATURE:
<223> OTHER INFORMATION: 26B12H3

<400> SEQUENCE: 15

Asp Val Gln Leu Gln Glu Ser Gly Pro Gly Leu Val Lys Pro Ser Gln
1               5                   10                  15

Thr Leu Ser Leu Thr Cys Thr Val Ser Gly His Ser Phe Thr Ser Asp
            20                  25                  30

Tyr Ala Trp Ser Trp Ile Arg Gln Pro Pro Gly Lys Gly Leu Glu Trp
        35                  40                  45

Ile Gly Tyr Ile Ser Tyr Ser Asp Ser Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Asp Tyr Gly Asn Tyr Gly Gly Ala Met Asp Tyr Trp Gly
            100                 105                 110

Gln Gly Thr Ser Val Thr Val Ser Ser
        115                 120

<210> SEQ ID NO 16
<211> LENGTH: 363
<212> TYPE: DNA
<213> ORGANISM: Artificial Sequence
<220> FEATURE:
<223> OTHER INFORMATION: 26B12H3

<400> SEQUENCE: 16
gatgtgcagc tgcaggagtc tggcccagga ctggtgaagc caagccagac cctgtccctg       60
acctgtacag tgtccggcca ctcttttaca agcgactacg cctggtcttg gatcagacag      120
ccccctggca agggactgga gtggatcggc tacatctcct attctgacag caccaactat      180
aatccctccc tgaagtctag agtgaccatc tctgtggata caagcaagaa ccagttctcc      240
ctgaagctga gctccgtgac cgcagcagac acagccgtgt actattgcgc ccggctggac      300
tacggcaatt atggcggagc catggattac tggggccagg gcaccagcgt gacagtgtct      360
agc                                                                    363

<210> SEQ ID NO 17
<211> LENGTH: 121
<212> TYPE: PRT
<213> ORGANISM: Artificial Sequence
<220> FEATURE:
<223> OTHER INFORMATION: 26B12H4

<400> SEQUENCE: 17

Asp Val Gln Leu Gln Glu Ser Gly Pro Gly Leu Val Lys Pro Ser Gln
1               5                   10                  15

Thr Leu Ser Leu Thr Cys Thr Val Ser Gly His Ser Phe Thr Ser Asp
            20                  25                  30

Tyr Ala Trp Asn Trp Ile Arg Gln Phe Pro Gly Lys Gly Leu Glu Trp
        35                  40                  45

Met Gly Tyr Ile Ser Tyr Ser Asp Ser Thr Asn Tyr Asn Pro Ser Leu
    50                  55                  60

Lys Ser Arg Ile Thr Ile Ser Arg Asp Thr Ser Lys Asn Gln Phe Phe
65                  70                  75                  80
```

```
Leu Gln Leu Asn Ser Val Thr Ala Ala Asp Thr Ala Thr Tyr Tyr Cys
            85                  90                  95

Ala Arg Leu Asp Tyr Gly Asn Tyr Gly Gly Ala Met Asp Tyr Trp Gly
            100                 105                 110

Gln Gly Thr Ser Val Thr Val Ser Ser
        115                 120
```

```
<210> SEQ ID NO 18
<211> LENGTH: 363
<212> TYPE: DNA
<213> ORGANISM: Artificial Sequence
<220> FEATURE:
<223> OTHER INFORMATION: 26B12H4

<400> SEQUENCE: 18
```

```
gatgtgcagc tgcaggagag cggccccgga ctggtgaagc cttcccagac cctgtctctg      60
acctgtacag tgtctggcca cagcttcaca tccgactacg cctggaactg gatcaggcag      120
tttccaggca agggcctgga gtggatgggc tacatctctt atagcgactc caccaactat      180
aatccctctc tgaagagccg gatcaccatc agcagagata catccaagaa ccagttcttt      240
ctgcagctga cagcgtgac agccgccgac accgccacat actattgcgc ccggctggac      300
tacggcaatt atggcggagc catggattac tggggccagg gcacctccgt gacagtgagc      360
tcc                                                                    363
```

```
<210> SEQ ID NO 19
<211> LENGTH: 107
<212> TYPE: PRT
<213> ORGANISM: Artificial Sequence
<220> FEATURE:
<223> OTHER INFORMATION: 26B12L1

<400> SEQUENCE: 19
```

```
Asp Ile Gln Met Thr Gln Ser Pro Lys Ser Leu Ser Thr Ser Val Gly
1               5                   10                  15

Asp Arg Val Thr Ile Thr Cys Arg Ser Ser Gln His Val Ser Thr Ala
            20                  25                  30

Val Ala Trp Tyr Gln Gln Lys Pro Gly Lys Ser Pro Lys Leu Leu Ile
            35                  40                  45

Tyr Ser Ala Ser Tyr Arg Tyr Ser Gly Val Pro Asp Arg Phe Ser Gly
        50                  55                  60

Ser Gly Ser Gly Thr Asp Phe Thr Phe Thr Ile Ser Ser Val Gln Pro
65                  70                  75                  80

Glu Asp Phe Ala Thr Tyr Tyr Cys Gln Gln His Tyr Ile Thr Pro Trp
                85                  90                  95

Thr Phe Gly Gly Gly Thr Lys Leu Glu Ile Lys
            100                 105
```

```
<210> SEQ ID NO 20
<211> LENGTH: 321
<212> TYPE: DNA
<213> ORGANISM: Artificial Sequence
<220> FEATURE:
<223> OTHER INFORMATION: 26B12L1

<400> SEQUENCE: 20
```

```
gacatccaga tgacccagtc ccctaagtcc ctgtctacaa gcgtgggcga tcgggtgacc      60
atcacatgta gaagctccca gcacgtgtct accgcagtgg catggtacca gcagaagcca      120
```

-continued

```
ggcaagagcc ctaagctgct gatctattcc gcctcttaca ggtattccgg agtgccagac       180
cggtttagcg gctccggctc tggcaccgat ttcacctttta caatctctag cgtgcagcca       240
gaggacttcg ccacatacta ttgccagcag cactacatca ccccatggac cttcggcggc       300
ggcacaaagc tggagatcaa g                                                  321
```

<210> SEQ ID NO 21
<211> LENGTH: 107
<212> TYPE: PRT
<213> ORGANISM: Artificial Sequence
<220> FEATURE:
<223> OTHER INFORMATION: 26B12L2

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln His Val Ser Thr Ala
            20                  25                  30

Leu Ala Trp Tyr Gln Gln Lys Pro Gly Lys Ser Pro Lys Leu Leu Ile
        35                  40                  45

Tyr Ser Ala Ser Ser Arg Tyr Ser Gly Val Pro Asp Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ile Thr Pro Trp
                85                  90                  95

Thr Phe Gly Gly Gly Thr Lys Leu Glu Ile Lys
            100                 105
```

<210> SEQ ID NO 22
<211> LENGTH: 321
<212> TYPE: DNA
<213> ORGANISM: Artificial Sequence
<220> FEATURE:
<223> OTHER INFORMATION: 26B12L2

<400> SEQUENCE: 22

```
gacatccaga tgacccagtc ccctagctcc ctgtctgcca gcgtgggcga tagggtgacc        60
atcacatgta gatctagcca gcacgtgtct acagccctgg catggtacca gcagaagcca       120
ggcaagagcc ctaagctgct gatctactcc gcctcctcta ggtattctgg agtgccagac       180 cggtttttccg gctctggcag cggcaccgat ttcacctttta caatcagctc cctgcagcca       240
gaggacttcg ccacatacta ttgccagcag cactatatca ccccatggac cttcggcggc       300
ggcaccaagc tggagatcaa g                                                  321
```

<210> SEQ ID NO 23
<211> LENGTH: 107
<212> TYPE: PRT
<213> ORGANISM: Artificial Sequence
<220> FEATURE:
<223> OTHER INFORMATION: 26B12L3

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln His Val Ser Thr Ala
            20                  25                  30

Leu Ala Trp Tyr Gln Gln Lys Pro Gly Lys Ala Pro Lys Leu Leu Ile
        35                  40                  45
```

```
Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ile Thr Pro Trp
                85                  90                  95

Thr Phe Gly Gly Gly Thr Lys Leu Glu Ile Lys
            100                 105
```

<210> SEQ ID NO 24
<211> LENGTH: 321
<212> TYPE: DNA
<213> ORGANISM: Artificial Sequence
<220> FEATURE:
<223> OTHER INFORMATION: 26B12L3

<400> SEQUENCE: 24

```
gacatccaga tgacccagtc ccctagctcc ctgagcgcct ccgtgggcga tagggtgacc       60
atcacatgta gagcctctca gcacgtgagc acagccctgg catggtacca gcagaagcca      120
ggcaaggccc ctaagctgct gatctatagc gcctctagcc tgcagtccgg agtgccatct      180
cggttctctg gcagcggctc cggaaccgac tttaccctga caatctcctc tctgcagcca      240
gaggatttcg ccacatacta ttgccagcag cactacatca ccccatggac cttcggcggc      300
ggcaccaagc tggagatcaa g                                                321
```

<210> SEQ ID NO 25
<211> LENGTH: 107
<212> TYPE: PRT
<213> ORGANISM: Artificial Sequence
<220> FEATURE:
<223> OTHER INFORMATION: 26B12L4

<400> SEQUENCE: 25

```
Asp Ile Gln Met Thr Gln Ser Pro Lys Ser Met Ser Thr Ser Val Gly
1               5                   10                  15

Asp Arg Val Thr Ile Thr Cys Arg Ser Ser Gln His Val Ser Thr Ala
                20                  25                  30

Val Ala Trp Tyr Gln Gln Lys Pro Gly Lys Ser Pro Lys Leu Leu Ile
            35                  40                  45

Tyr Ser Ala Ser Tyr Arg Tyr Ser Gly Val Pro Asp Arg Phe Ser Gly
    50                  55                  60

Ser Gly Ser Gly Thr Asp Phe Thr Phe Thr Ile Ser Ser Val Gln Pro
65                  70                  75                  80

Glu Asp Phe Ala Thr Tyr Tyr Cys Gln Gln His Tyr Ile Thr Pro Trp
                85                  90                  95

Thr Phe Gly Gly Gly Thr Lys Leu Glu Ile Lys
            100                 105
```

<210> SEQ ID NO 26
<211> LENGTH: 321
<212> TYPE: DNA
<213> ORGANISM: Artificial Sequence
<220> FEATURE:
<223> OTHER INFORMATION: 26B12L4

<400> SEQUENCE: 26

```
gacatccaga tgacccagtc ccctaagtcc atgtctacaa gcgtgggcga cagggtgacc       60
atcacatgta gaagctccca gcacgtgtct accgcagtgg catggtacca gcagaagcca      120
```

-continued

```
ggcaagagcc ctaagctgct gatctattcc gcctcttaca ggtattccgg agtgccagac    180
cggtttagcg gctccggctc tggcaccgat ttcacctttta caatctctag cgtgcagcca    240
gaggacttcg ccacatacta ttgccagcag cactacatca ccccatggac cttcggcggc    300
ggcacaaagc tggagatcaa g                                              321
```